United States Patent
Huang

(10) Patent No.: US 9,943,384 B2
(45) Date of Patent: Apr. 17, 2018

(54) SELF-LIGATING ORTHODONTIC BRACKET AND METHOD OF USING SAME

(71) Applicant: Ormco Corporation, Orange, CA (US)

(72) Inventor: Stanley S. Huang, Irvine, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 15/372,663

(22) Filed: Dec. 8, 2016

(65) Prior Publication Data

US 2017/0086949 A1 Mar. 30, 2017

Related U.S. Application Data

(63) Continuation of application No. 14/205,674, filed on Mar. 12, 2014, now Pat. No. 9,532,853.

(60) Provisional application No. 61/798,675, filed on Mar. 15, 2013.

(51) Int. Cl.
  *A61C 3/00* (2006.01)
  *A61C 7/28* (2006.01)
  *A61C 7/30* (2006.01)

(52) U.S. Cl.
  CPC ............... *A61C 7/287* (2013.01); *A61C 7/30* (2013.01)

(58) Field of Classification Search
  CPC .. A61C 7/287; A61C 7/30; A61C 7/12; A61C 7/14; A61C 7/141; A61C 7/16; A61C 7/06
  USPC .................. 433/11, 8, 9, 10, 13, 18
  See application file for complete search history.

(56) References Cited

U.S. PATENT DOCUMENTS

| | | | |
|---|---|---|---|
| 4,103,423 A | * | 8/1978 | Kessel ............... A61C 7/285 433/10 |
| 4,492,573 A | | 1/1985 | Hanson |
| 5,094,614 A | | 3/1992 | Wildman |
| 5,275,557 A | | 1/1994 | Damon |

(Continued)

FOREIGN PATENT DOCUMENTS

| | | |
|---|---|---|
| EP | 1063936 A1 | 1/2001 |
| EP | 1508310 A2 | 2/2005 |

(Continued)

OTHER PUBLICATIONS

United States Patent and Trademark Office, Office Action issued in U.S. Appl. No. 12/752,411, dated Jul. 12, 2013.

(Continued)

*Primary Examiner* — Cris L Rodriguez
*Assistant Examiner* — Mirayda A Aponte
(74) *Attorney, Agent, or Firm* — Wood Herron & Evans LLP

(57) ABSTRACT

A self-ligating orthodontic bracket includes a bracket body, a slide member, and a resilient member. The slide member is movable relative to the bracket body between an opened position, a first ligating position, and a second ligating position. In the first ligating position and in the second ligating position, a surface of the slide member bounds the archwire slot on a side generally opposite to the base surface to retain the archwire. The resilient member is configured to engage the other of the slide member and the bracket body and has a deformed state for biasing the slide member toward the base surface in at least one of the first and second ligating positions. In the first and second ligating positions, the base surface of the archwire slot and the surface of the slide member are separated by different distances.

24 Claims, 12 Drawing Sheets

(56) References Cited

U.S. PATENT DOCUMENTS

| | | | |
|---|---|---|---|
| 5,322,435 A | 6/1994 | Pletcher | |
| 5,356,288 A | 10/1994 | Cohen | |
| 5,466,151 A | 11/1995 | Damon | |
| 5,474,445 A * | 12/1995 | Voudouris | A61C 7/285 433/10 |
| 5,857,849 A | 1/1999 | Kurz | |
| 5,857,850 A | 1/1999 | Voudouris | |
| 5,971,753 A | 10/1999 | Heiser | |
| 6,071,118 A | 6/2000 | Damon | |
| 6,071,119 A | 6/2000 | Christoff et al. | |
| 7,674,110 B2 * | 3/2010 | Oda | A61C 7/285 433/10 |
| 7,857,618 B2 | 12/2010 | Abels et al. | |
| 7,963,768 B2 | 6/2011 | Hilliard | |
| 2006/0154196 A1 | 7/2006 | Oda | |
| 2007/0224569 A1 | 9/2007 | Oda | |
| 2007/0248928 A1 | 10/2007 | Damon | |
| 2007/0269763 A1 | 11/2007 | Schendell-Groling | |
| 2008/0045956 A1 | 2/2008 | Songer et al. | |
| 2010/0285420 A1 | 11/2010 | Oda | |
| 2012/0064476 A1 | 3/2012 | Sabilla | |
| 2012/0288816 A1 | 11/2012 | Dupray et al. | |

FOREIGN PATENT DOCUMENTS

| | | |
|---|---|---|
| WO | 2011062603 A1 | 5/2011 |
| WO | 2012145144 A1 | 10/2012 |

OTHER PUBLICATIONS

United States Patent and Trademark Office, Office Action issued in U.S. Appl. No. 12/752,411, dated Aug. 21, 2012.
United States Patent and Trademark Office, Office Action issued in U.S. Appl. No. 12/752,411, dated Oct. 27, 2011.
European Patent and Trademark Office, European Search Report in EP Application No. 10250843, dated Mar. 7 2011.
European Patent and Trademark Office, European Search Report in EP Application No. 13191984.7, dated Mar. 3, 2014.
European Patent and Trademark Office, European Search Report in EP Application No. 14159463, dated Jul. 1, 2014.
European Patent Office, European Search Report in EP15200217.6 dated Apr. 26, 2016.

* cited by examiner

US 9,943,384 B2

SELF-LIGATING ORTHODONTIC BRACKET AND METHOD OF USING SAME

CROSS REFERENCE TO RELATED APPLICATIONS

This application is a continuation of U.S. patent application Ser. No. 14/205,674 filed Mar. 12, 2014, which claims priority to U.S. Provisional Patent Application Ser. No. 61/798,675 filed Mar. 15, 2013, the disclosures of which is incorporated by reference herein in its entirety.

TECHNICAL FIELD

The invention relates generally to orthodontic brackets and, more particularly, to self-ligating orthodontic brackets and methods of using those brackets in orthodontic treatment.

BACKGROUND

Orthodontic brackets represent a principal component of all corrective orthodontic treatments devoted to improving a patient's occlusion. In conventional orthodontic treatments, an orthodontist or an assistant affixes brackets to the patient's teeth and engages an archwire into a slot of each bracket. The archwire applies corrective forces that coerce the teeth to move into correct positions. Traditional ligatures, such as small elastomeric O-rings or fine metal wires, are employed to retain the archwire within each bracket slot. Due to difficulties encountered in applying an individual ligature to each bracket, self-ligating orthodontic brackets have been developed that eliminate the need for ligatures by relying on a movable portion or member, such as a latch or slide, for retaining the archwire within the bracket slot.

There are generally two types of ligation of the archwire to the orthodontic bracket: passive ligation and active ligation. In passive ligation, a closure member bounds the archwire slot such that the archwire slot has a fixed width dimension (e.g., labially-lingually). Additionally, the archwire located in the archwire slot typically has a width dimension that is smaller than the width dimension such that there is a space or gap between the archwire and the archwire slot.

In contrast, in active ligation, an aspect of the bracket actively imposes a force onto the archwire to seat the archwire within the archwire slot such that there are generally no spaces or gaps and a snug fit is attained therebetween. The biasing of the archwire into the archwire slot may be achieved, for example, through the use of a resilient member on the bracket that acts on the archwire to push the archwire towards the base of the archwire slot.

During the early stages of orthodontic treatment, significant movement of the teeth is generally desired. This typically requires there to be significant movement of the archwire relative to the brackets on the teeth. Accordingly, during these early stages of treatment, passive ligation of the archwire may be desired to facilitate the relative movement between archwire and the brackets during these relatively large movements of the teeth. To achieve passive ligation, relatively small or thin archwires are often used to ensure sufficient space in the archwire slot.

During the finishing stages of orthodontic treatment, however, fine and precise movements of the teeth may be desired. These movements typically require excellent control of the archwire within the archwire slot. Thus, during these final stages of treatment, active ligation of the archwire may be desired to facilitate, for example, excellent torque and rotational control of the teeth. To achieve active ligation, generally large or thick archwires are often used to ensure a snug fit in the archwire slot.

While orthodontic treatment often proceeds according to the above treatment plan, i.e., passive ligation during early stages and active ligation during final stages, it may be desirable in some cases to deviate from that treatment plan. By way of example, when using a certain size archwire (e.g., a threshold size of archwire), it may be desirable to give the orthodontist or the clinician the option of selecting the type of ligation he or she desires for securing the archwire to the bracket. This may allow for greater variability in the treatment plan to meet the specific needs of any particular patient. Current orthodontic brackets, however, and especially self-ligating orthodontic brackets, typically do not provide the ability for the orthodontist to select between active and passive ligation of the archwire in an efficient and straight forward manner.

Thus, while self-ligating brackets have been generally successful, manufacturers of such brackets continually strive to improve their use and functionality. In this regard, there remains a need for self-ligating orthodontic brackets that allow an orthodontist or clinician to select between active and passive ligation of the archwire in an improved manner. In this way, orthodontists may develop treatment plans that more adequately meet the needs of patients.

SUMMARY OF THE INVENTION

The present invention overcomes the foregoing and other shortcomings and drawbacks of orthodontic brackets. While the present invention will be described in connection with certain embodiments, it will be understood that the present invention is not limited to these embodiments. On the contrary, the present invention includes all alternatives, modifications and equivalents as may be included within the spirit and scope of the present invention.

In accordance with the principles of the present invention, an orthodontic bracket for coupling an archwire with a tooth comprises a bracket body configured to be mounted to the tooth. The bracket body includes an archwire slot that is configured to receive the archwire therein and has a base surface that at least partly defines the archwire slot. The orthodontic bracket further comprises a slide member that is engaged with the bracket body and that is movable relative to the bracket body between an opened position, a first ligating position, and a second ligating position. In the opened position, the archwire is insertable into the archwire slot. In the first ligating position and in the second ligating position, a surface of the slide member bounds the archwire slot on a side generally opposite to the base surface to retain the archwire in the archwire slot. The orthodontic bracket further comprises a resilient member coupled to one of the slide member and the bracket body. The resilient member is configured to engage the other of the slide member and the bracket body. The resilient member has a deformed state that is configured to impose a force that biases the slide member toward the base surface of the archwire slot in at least one of the first and second ligating positions. In the first ligating position, the base surface of the archwire slot and the surface of the slide member are separated by a first distance, and in the second ligating position, the base surface of the archwire slot and the slide member are separated by a second distance that is different from the first distance.

According to one aspect of the present invention, the resilient member is deformed when in the first ligating position such that the slide member is biased toward the base surface of the archwire slot when the slide member is in the first ligating position. The first distance may be less than the second distance.

According to one aspect of the present invention, the force biasing the slide member toward the base surface of the archwire slot is greater in the first ligating position than in the second ligating position.

According to one aspect of the present invention, the resilient member is deformed when in the second ligating position such that the slide member is biased toward the base surface of the archwire slot when in the second ligating position. The second distance may be less than the first distance.

According to one aspect of the present invention, the force biasing the slide member toward the base surface of the archwire slot is greater in the second ligating position than in the first ligating position.

According to one aspect of the present invention, movement of the slide member between the opened position, the first ligating position, and the second ligating position is along a ligating axis that is generally perpendicular to an axis of the archwire slot.

According to one aspect of the present invention, a distance of travel of the slide member generally perpendicular to an axis of the archwire slot from the opened position to the first ligating position is less than a distance of travel of the slide member generally perpendicular to the axis of the archwire slot from the opened position to the second ligating position.

According to one aspect of the present invention, the resilient member includes a spring pin.

According to one aspect of the present invention, the slide member engages a portion of the bracket body on both sides of the archwire slot when in the second ligating position.

According to one aspect of the present invention, the archwire slot further includes a first slot surface and a second slot surface extending outwardly from the base surface and the slide member has a leading edge that is adjacent the first slot surface in the opened position, between the first slot surface and the second slot surface in the first ligating position, and adjacent the second slot surface in the second ligating position.

According to one aspect of the present invention, the surface of the slide member is fixed relative to the base surface of the archwire slot in each of the first ligating position and the second ligating position.

According to one aspect of the present invention, the bracket body includes a wall and the slide member contacts the wall in one of the first ligating position and the second ligating position. The wall is configured to define a minimum distance between the base surface of the archwire slot and the surface of the slide member. The slide member may be configured to contact the wall in the first position. Alternatively, the slide member may be configured to contact the wall in the second position.

In accordance with the principles of the present invention, a method of orthodontic treatment with a self-ligating orthodontic bracket attached to a tooth, the orthodontic bracket including a bracket body having an archwire slot formed therein, a slide member, and a resilient member coupled to one of the slide member and the bracket body and configured to engage the other of the slide member and the bracket body, and an archwire being disposed in the archwire slot, the method comprises moving the slide member generally perpendicularly toward an axis of the archwire slot from a first ligating position to a second ligating position. In the first ligating position, a surface of the slide member is spaced from a base surface of the archwire slot at a first distance. The surface of the slide member opposes the base surface of the archwire slot so as to form one boundary of the archwire slot and inhibits the archwire from being removed from the archwire slot. In the second ligating position, the surface of the slide member is spaced from the base surface of the archwire slot at a second distance that is different from the first distance, forms one boundary of the archwire slot, and inhibits the archwire from being removed from the archwire slot. In one of the first ligating position and the second ligating position, the resilient member has a deformed state that biases the slide member toward the base surface of the archwire slot.

According to one aspect of the present invention, the first ligating position includes active ligation of the archwire, and the second ligating position includes passive ligation of the archwire, and moving the slide member includes moving the slide member from active ligation of the archwire to passive ligation of the archwire.

According to one aspect of the present invention, the first ligating position includes passive ligation of the archwire and the second ligating position includes active ligation of the archwire, and moving the slide member includes moving the slide member from passive ligation of the archwire to active ligation of the archwire.

According to one aspect of the present invention, moving the slide member includes moving the surface of the slide member closer to the base surface of the archwire slot.

According to one aspect of the present invention, moving the slide member includes moving the surface of the slide member further from the base surface of the archwire slot.

According to one aspect of the present invention, the method further comprises moving the slide member from the first ligating position to an opened position in which the archwire slot is open, and removing the archwire from the archwire slot.

According to one aspect of the present invention, moving the slide member from the first ligating position to the opened position includes moving the slide member generally perpendicularly away from the axis of the archwire slot.

The above and other objectives and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the detailed description given below, serve to explain the invention.

DETAILED DESCRIPTION

Although the invention will be described in connection with certain embodiments, the invention is not limited to practice in any one specific type of self-ligating orthodontic bracket. The description of the embodiments of the invention is intended to cover all alternatives, modifications, and equivalent arrangements as may be included within the spirit and scope of the invention as defined by the appended claims. In particular, those skilled in the art will recognize that the components of the embodiments of the invention described herein could be arranged in multiple different ways.

With reference generally to the figures, embodiments of the present invention include a self-ligating orthodontic bracket having an archwire slot and a movable member movable relative to the archwire slot to an opened position in which an orthodontic archwire may be inserted into the archwire slot. The movable member may then be moved to one or more closed positions in which the archwire is captured within the archwire slot. The closed positions may include at least two positions that capture the archwire within the archwire slot. However, the closed positions differ in their relative position with respect to the archwire slot so as to provide two different effective dimensions of the archwire slot.

In use, it is contemplated that a clinician may operate the movable member between the at least two closed positions to change the effective dimension of the archwire slot. In particular, the clinician may operate the movable member to a first closed position in which the bracket actively ligates an archwire in the archwire slot and then move the movable member to a second closed position in which the bracket passively ligates the archwire, without changing the archwire. In this situation, the clinician may alter the ligation mode (i.e., active or passive) without changing the archwire. Alternatively, the clinician may move the movable member between a first closed position, in which the bracket passively ligates the archwire, and a second closed position in which the bracket actively ligates the archwire. In this sense, the self-ligating brackets according to embodiments of the present invention are configured to operate in either the active mode or the passive mode and be capable of switching between the modes by movement of the movable member and without changing the archwire or adding a ligature or another device.

Figure 1:
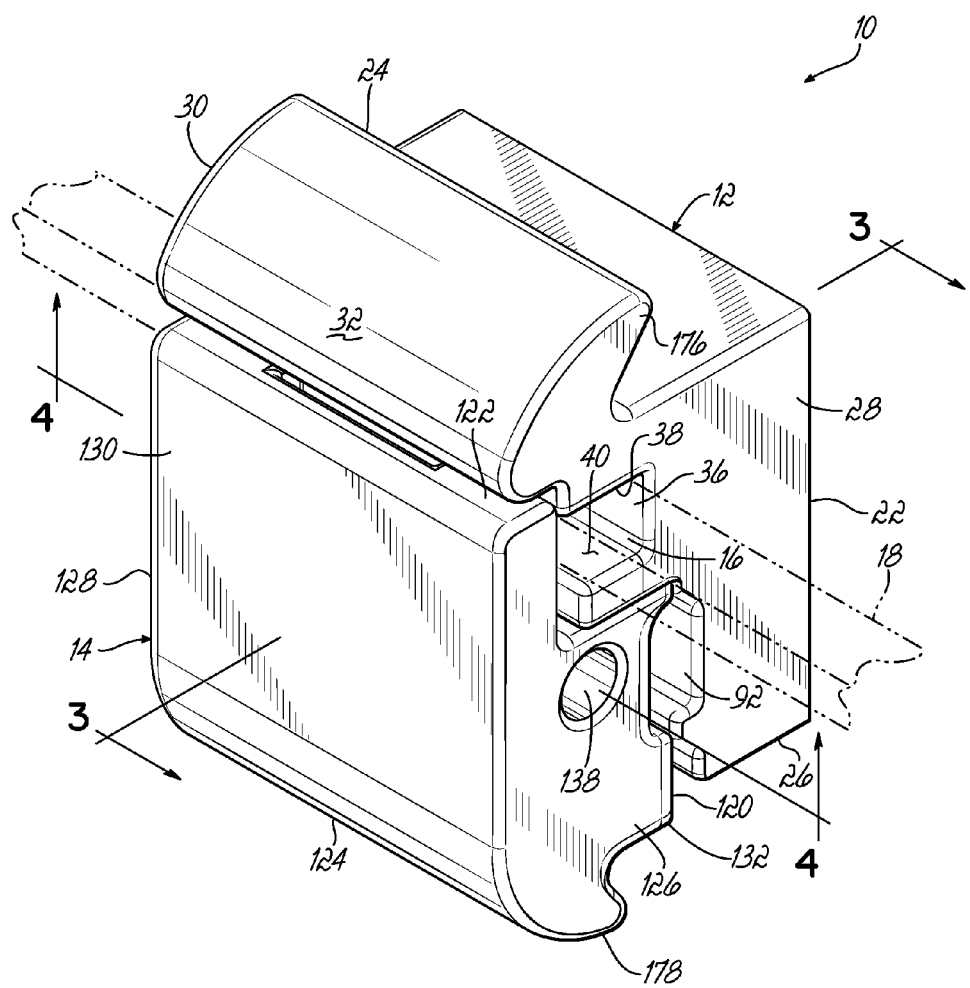
FIG. 1 is a perspective view of an orthodontic bracket according to one embodiment of the invention, a slide member shown in the passive position.
Figure 2:
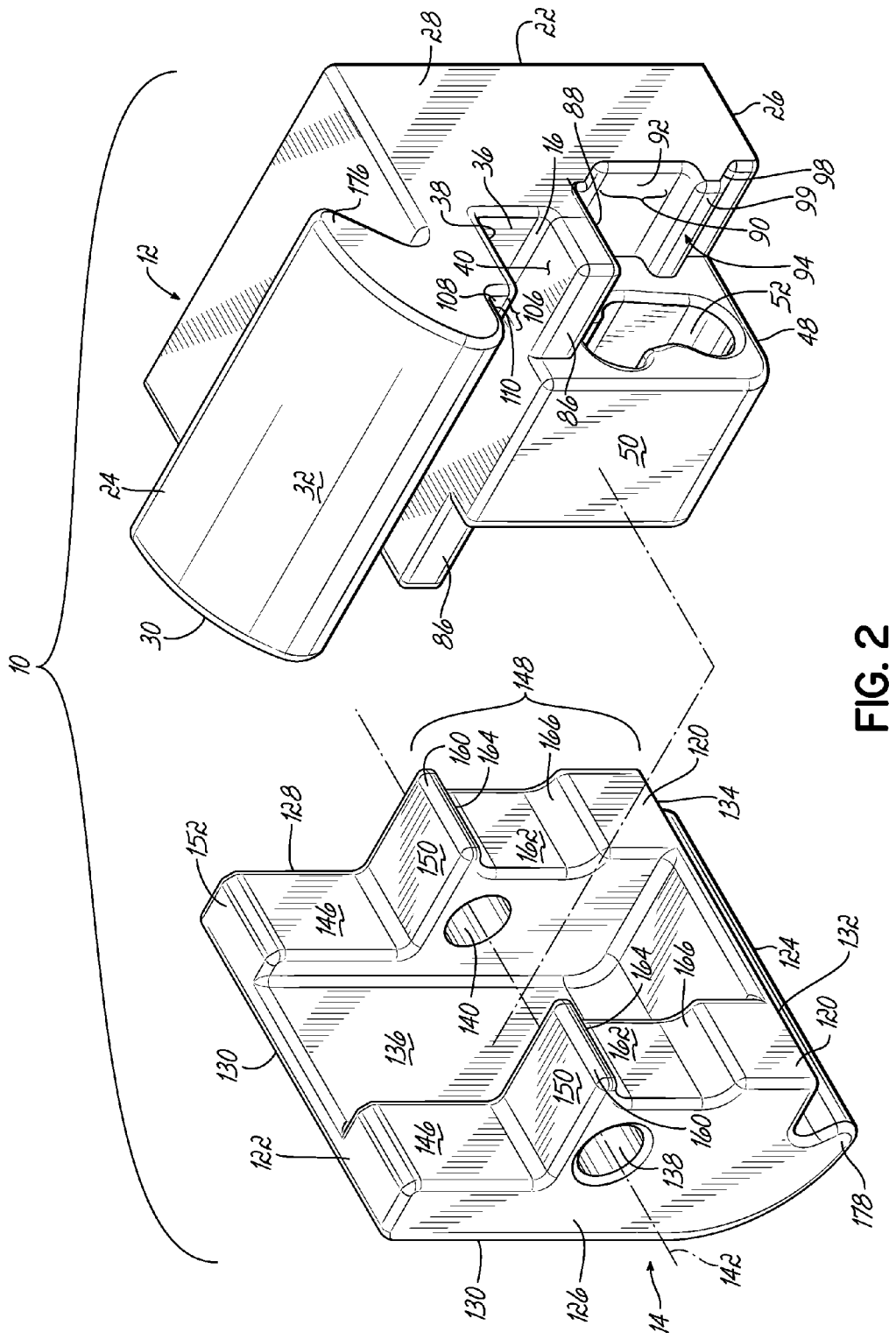
FIG. 2 is an exploded perspective view of the orthodontic bracket shown in FIG. 1.

To that end and referring now to the drawings, and to FIGS. 1 and 2 in particular, an orthodontic bracket 10 includes a bracket body 12 and a movable closure member coupled to the bracket body 12. In one embodiment, the movable closure member may include a ligating slide 14 slidably coupled with the bracket body 12. While the movable closure member is described herein as a ligating slide, the invention is not so limited as the movable closure member may include other movable structures (e.g., latch, spring clip, door, etc.). The bracket body 12 includes an archwire slot 16 formed therein configured to receive an archwire 18 (shown in phantom) for applying corrective forces to the teeth. The ligating slide 14 is movable between an opened position (e.g., FIG. 3A) in which the archwire 18 is insertable into the archwire slot 16; a first ligating position (e.g., FIG. 3B), in which the archwire 18 is retained in the archwire slot 16 and ligated to the bracket body 12 in one of an active or passive manner; and a second ligating position (e.g., FIG. 3C), in which the archwire 18 is retained in the archwire slot 16 and ligated to the bracket body 12 in the other of the active or passive manner. For example, in the embodiment shown in FIGS. 1-4, the first ligating position may be an active ligating position, and the second ligating position may be a passive ligating position. Alternatively, and as shown in FIGS. 5-7C, the first ligating position may be a passive ligating position, and the second ligating position may be an active ligating position. In any event, the bracket body 12 and ligating slide 14 collectively form an orthodontic bracket 10 for use in corrective orthodontic treatments.

In addition to the above, the orthodontic bracket 10 further includes a multi-function biasing member coupled to one of the bracket body 12 or ligating slide 14 and configured to engage the other of the bracket body 12 or ligating slide 14. For example, as explained in more detail below, the biasing member, which in one embodiment includes a resilient member 20 (shown in FIGS. 3A-3C), provides a force for biasing the ligating slide 14 toward the base of the archwire slot 16 in at least one of the first and second ligating positions. More particularly, the biasing member provides a force for biasing the ligating slide 14 toward the base of the archwire slot 16 at least when the slide is in the active ligating position. In one embodiment, for example, the resilient member 20 may include a tubular pin. In this regard, the cross section may be continuous, that is, the tubular resilient member 20 may be without slots or other discontinuities in its sidewall. In this regard, and unlike a slotted tubular spring pin, the perimeter of the resilient member 20 is generally maintained when the resilient member 20 is elastically deformed. While the biasing member is described herein as a resilient member (e.g., tubular pin), the invention is not so limited as other biasing members may be configured for use in embodiments in accordance with the invention.

Moreover, resilient member 20 may further provide a retaining feature for retaining the ligating slide 14 to the bracket body 12 such that the ligating slide 14 cannot be separated therefrom during use. As will be discussed below, in one embodiment, the biasing member may be configured to engage an aspect of the bracket body 12 to prevent the ligating slide 14 from being separated from the bracket body 12. Furthermore, the resilient member 20 may provide a securing mechanism for securing the ligating slide 14 in at least the first and second ligating positions. As will be discussed below, in one embodiment, the biasing member may be configured to engage aspects of the bracket body 12 such that a threshold level of force must be applied to the ligating slide 14 before the ligating slide 14 may be moved away from the first ligating position or the second ligating position. In an exemplary embodiment, the same resilient member facilitates all of these various functions.

In an exemplary embodiment, the resilient member 20 may be composed of Nickel Titanium (NiTi) superelastic material. By way of example, one NiTi composition includes about 55 wt. % nickel (Ni), and about 45 wt. % titanium (Ti) with minor amounts of impurities and which is available from NDC of Fremont, Calif. The mechanical properties of the NiTi alloy may include an ultimate tensile strength of greater than about 155 ksi, an upper plateau of greater than about 55 ksi, and a lower plateau of greater than about 25 ksi. The dimensions of the resilient member 20 may vary depending on the size of the bracket 10. In one embodiment, the resilient member 20 is a generally right circular hollow cylinder having a diameter of about 0.016 inch and being from about 0.050 inch to about 0.125 inch in length. The sidewall thickness may measure from about 0.001 inch to about 0.004 inch, and may preferably be about 0.002 inch to about 0.003 inch.

The orthodontic bracket 10, unless otherwise indicated, is described herein using a reference frame attached to a labial surface of a tooth on the lower jaw. Consequently, as used herein, terms such as labial, lingual, mesial, distal, occlusal, and gingival used to describe bracket 10 are relative to the chosen reference frame. The embodiments of the invention, however, are not limited to the chosen reference frame and descriptive terms, as the orthodontic bracket 10 may be used on other teeth and in other orientations within the oral cavity. For example, the bracket 10 may also be coupled to the lingual surface of the tooth and be within the scope of the invention. Those of ordinary skill in the art will recognize that the descriptive terms used herein may not directly apply when there is a change in reference frame. Nevertheless, embodiments of the invention are intended to be independent of location and orientation within the oral cavity and the relative terms used to describe embodiments of the orthodontic bracket are to merely provide a clear description of the embodiments in the drawings. As such, the relative terms labial, lingual, mesial, distal, occlusal, and gingival are in no way limiting the invention to a particular location or orientation.

When mounted to the labial surface of a tooth T (not shown) carried on the patient's lower jaw and with reference specifically to FIG. 1, the bracket body 12 has a lingual side 22, an occlusal side 24, a gingival side 26, a mesial side 28, a distal side 30 and a labial side 32. The lingual side 22 of the bracket body 12 is configured to be secured to the tooth in any conventional manner, such as for example, by an appropriate orthodontic cement or adhesive or by a band around an adjacent tooth. In one embodiment, the lingual side 22 may further be provided with a pad (not shown) defining a bonding base that is secured to the surface of the tooth T. With reference to FIGS. 1 and 2, the bracket body 12 includes a base surface 36 and a pair of opposed slot surfaces 38, 40 projecting labially from the base surface 36 that collectively define the archwire slot 16, which may extend in a mesial-distal direction from mesial side 28 to distal side 30. The base surface 36 and slot surfaces 38, 40 are substantially encapsulated or embedded within the material of the bracket body 12 and are configured to receive the archwire 18 therein.

As shown in FIG. 2, in one embodiment, the bracket body 12 further includes a slide support portion 48 configured to receive the ligating slide 14 thereon. The slide support portion 48 may generally project labially from or be oriented generally perpendicular to the lingual side 22 of the bracket body 12. The slide support portion 48 generally defines a support surface 50 that may slidably engage the ligating slide 14 over at least a portion of its translational motion from at least one of the first and second ligating positions to the opened position. In a labial application (FIG. 1), the support surface 50 is positioned gingivally of the archwire slot 16 and extends in a generally occlusal-gingival direction.

With continued reference to FIG. 2, the slide support portion 48 includes an aperture 52 formed as a through bore in the mesial-distal direction. For example, in one embodiment, the aperture 52 may take the form of a closed slot through slide support portion 48. The aperture 52 may be positioned so that the longitudinal axis of the resilient member 20 extends generally parallel to the archwire slot 16 and in the mesial-distal direction.

In one embodiment, the aperture 52 is a generally asymmetrical bore that may be described as having an irregular configuration. The particular configuration of the aperture 52 is dictated by the desired ligation when the ligating slide is in the first and second ligating positions. In this regard, cooperation between the resilient member 20 in the aperture 52 may require intentional application of force to close the ligating slide 14. A minimum threshold force may be required on the ligating slide 14 to move it toward the active and passive positions. In one embodiment, the minimum threshold force is greater than the sliding weight of the ligating slide 14. In this embodiment, only when the force on the ligating slide 14 exceeds the minimum threshold force does the resilient member 20 move toward the active and passive positions. Forces on the ligating slide 14 that exceed the minimum threshold force cause the resilient member 20 to elastically deform. By elastic deformation, the strain produced in the resilient member 20 is fully recovered, and the member 20 reverts to its original shape, upon removal of the deforming force.

As will be described in detail below, the aperture 52 is configured to slidably engage the resilient member 20 to bias the ligating slide 14 toward the base surface 36 of the archwire slot 16 at least when the ligating slide 14 is in the active ligating position. For example, in one embodiment, the ligating slide 14 is configured to move relative to the bracket body 12 in a direction generally perpendicular to the direction of the archwire slot 16. For example, the ligating slide 14 may generally move in a gingival-occlusal direction. Additionally, the ligating slide 14 may move relative to the bracket body 12 from the opened position to the first ligating position, then to the second ligating position in a serial or sequential manner. In any event, the resilient member 20 biases the ligating slide 14 in a direction generally perpendicular to the slide translational movement and in a direction generally perpendicular to the archwire slot 16. In particular, when the ligating slide 14 is in at least the first ligating position, the resilient member 20 and the aperture 52 cooperate to bias the ligating slide 14 toward the base surface 36 of the archwire slot 16 (which may be generally in the lingual direction).

Figure 3A:
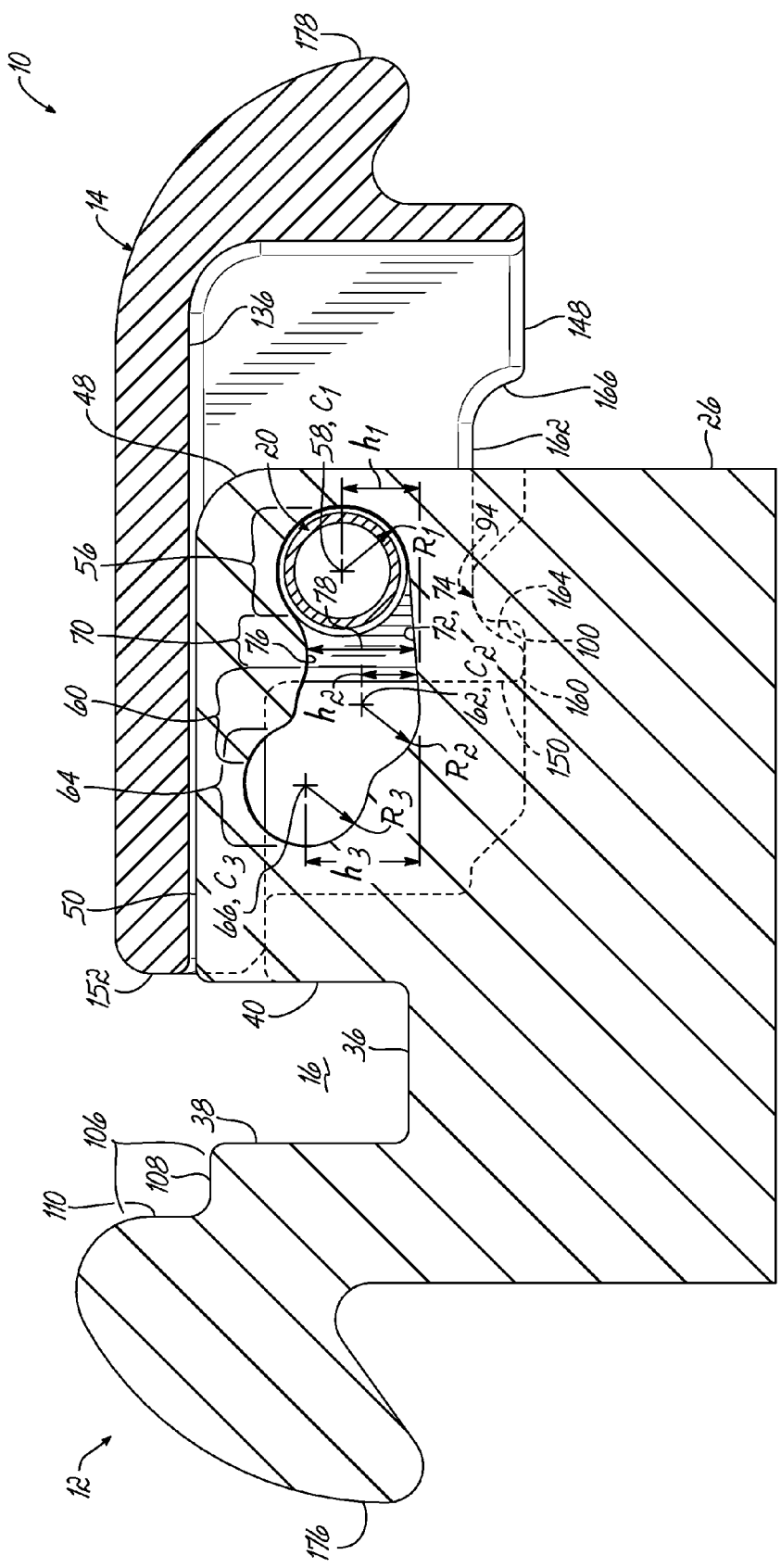
FIG. 3A is a cross-sectional view of the orthodontic bracket taken along section line 3-3 of FIG. 1, depicting the slide member in the opened position.
Figure 3B:
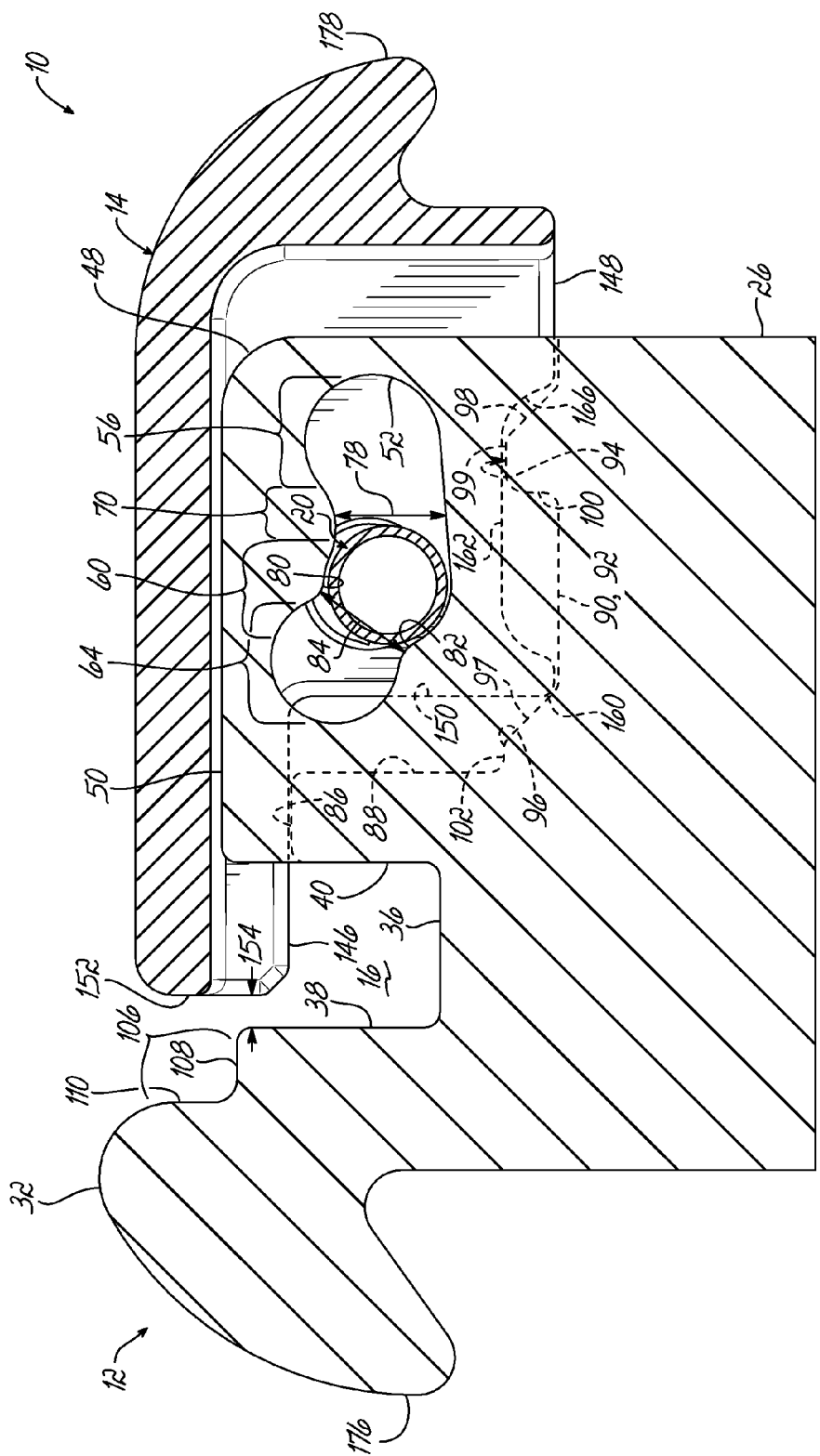
FIG. 3B is a cross-sectional view of the orthodontic bracket taken along section line 3-3 of FIG. 1, depicting the slide member in the active position.
Figure 3C:
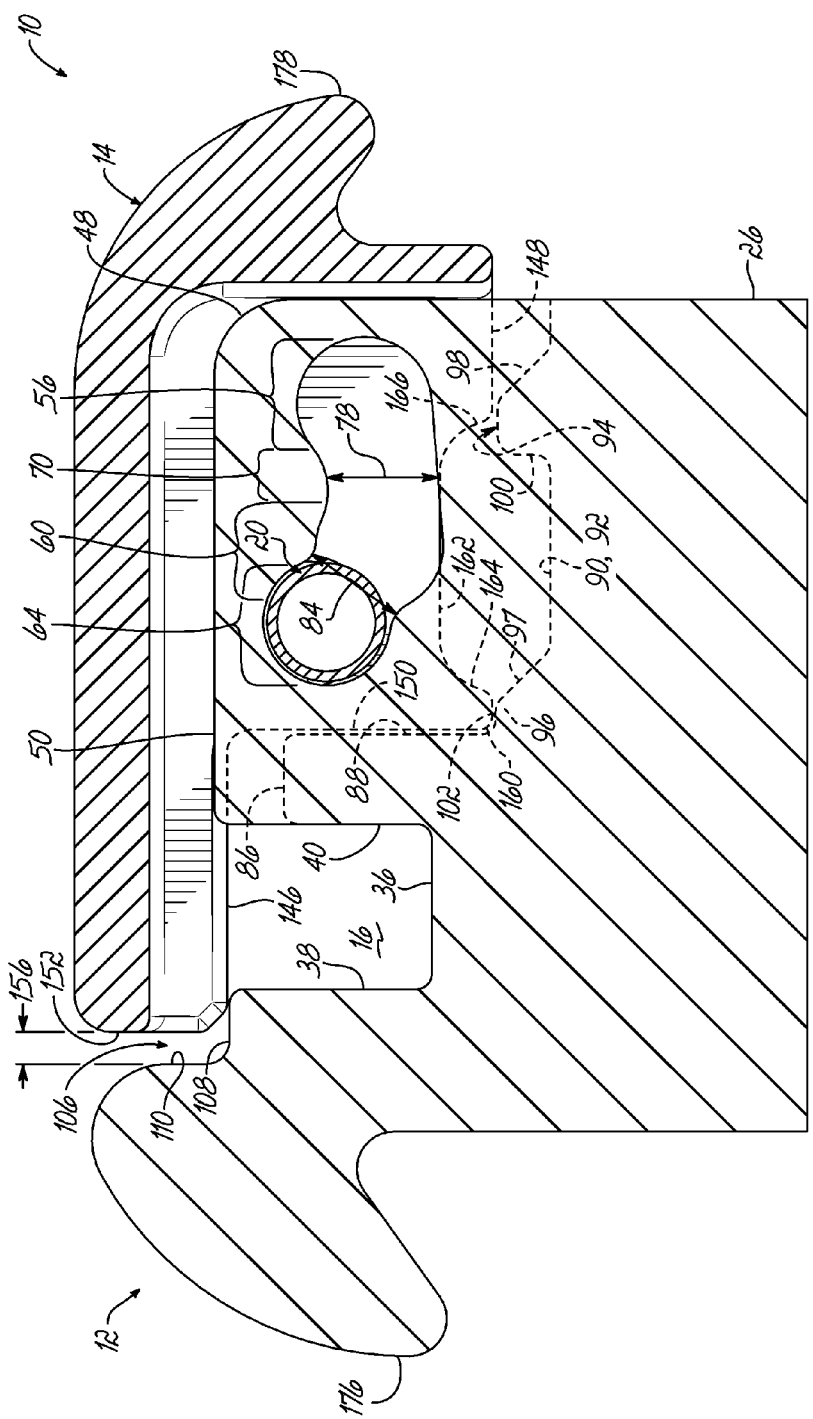
FIG. 3C is a cross-sectional view of the orthodontic bracket taken along section line 3-3 of FIG. 1, depicting the slide member in the passive position.

As shown in FIGS. 3A-3C, the aperture 52 may include a first lobe portion 56 proximate the gingival side 26. By way of example only, the first lobe portion 56 may define a generally circular perimeter along a portion of the aperture 52. The lobe portion 56 may be defined by an axis 58 and a radius R1. The lobe portion 56 may have a center C1 located a height h1 relative to the base surface 36 of the bracket body 12. The aperture 52 may further include a second lobe portion 60 positioned occlusally relative to the first lobe portion 56. Similar to the first lobe portion 56, the second lobe portion 60 may be defined by a generally circular perimeter having axis 62 and a radius R2. The second lobe portion 60 may have a center C2 located at a height h2 relative to the base surface 36 of the bracket body 12, where h1 is not equal to h2. In one embodiment, the height h2 is less than height h1. The aperture 52 may still further include a third lobe portion 64 positioned occlusally relative to the second lobe portion 60, such that the lobe portion 64 is proximate the archwire slot 16. Similar to the first and second lobe portions 56, 60, the third lobe portion 64 may be defined by a generally circular perimeter having axis 66 and radius R3. The third lobe portion 64 may have a center C3 located at a height h3 relative to the base surface 36 of the bracket body 12, where h3 is not equal to either of h1 or h2. In one embodiment, the height h3 may be greater than the height h2. In another embodiment, the height h3 may be greater than both of the heights h2 and h1. It should be appreciated that the relative heights of the first, second, and third lobe portions 56, 60, 64 may be dictated by the type and magnitude of the ligation desired at the opened and first and second ligating positions.

In one embodiment, the aperture 52 may include a central portion 70 positioned between and connecting the first lobe portion 56 and the second lobe portion 60. The central portion 70 may include a first segment 72 that is generally tangent to the first lobe portion 56 and that is also generally tangent to the second lobe portion 60. The first lobe portion 56, the second lobe portion 60 and the first segment 72 may generally define a portion of a slide track 74.

In addition, the central portion 70 may include a second segment 76 opposite the first segment 72. The second segment 76 may be generally tangent to the first lobe portion 56, but may extend in a direction such that an extension of the second segment 76 would intersect (rather than be tangent to) the second lobe portion 60.

In one embodiment, the orientation of the first segment 72 and the second segment 76 of the central portion 70 forms a restriction or pinch point 78 between the first lobe portion 56 and the second lobe portion 60. The pinch point 78 is generally a narrowing of the aperture 52 between the first and second lobe portions 56, 60. Elastic deformation of the resilient member 20 is dictated by the shape of the central portion 70, particularly the pinch point 78, of the aperture 52. In this regard, elastic deformation of member 20 may be localized to a region of contact with at least the pinch point 78. The pinch point 78 may include narrowing of the aperture 52 to a dimension that is less than each of the largest height (or labial-lingual) dimensions for the first and second lobe portions 56, 60, and is less than the diameter of the resilient member 20. Thus, generally the dimensions of the aperture 52 disclosed herein are ultimately determined by the dimensions of the resilient member 20. A smaller diameter resilient member 20 will generally be received in a correspondingly smaller aperture 52.

By way of example only and not limitation, where each of the first and second lobe portions 56, 60 generally define circular bores having radii R1 and R2, respectively, the pinch point 78 may be measured as a perpendicular distance between the first segment 72 and the nearest opposing portion of the central portion 70. This perpendicular distance may be less than the diameter of the first lobe portion 56 or less than the diameter of the second lobe portion 60 or less than each of the diameters of the first lobe portion 56 and the second lobe portion 60. Further, this dimension may be at least 5% less or in the range of about 10% to about 20% less than either diameter of the first or second lobe portions 58, 60. In one embodiment, the radius R2 is less than the radius R1 and the pinch point 78 is sized to be less than twice R2. By way of example and not limitation, radius R2 may be about 5% to about 15% less than radius R1. In an exemplary embodiment, the radius R1 may be about 0.010 inch and the radius R2 may be about 0.009 inch and the pinch point 78 may measure about 0.017 inch.

The configuration of the aperture 52, particularly the pinch point 78, controls the movement of the ligating slide from the opened position, shown in FIG. 3A, to the active position, shown in FIG. 3B. In this regard, when a force on the ligating slide 14 exceeds the minimum threshold force required to move the ligating slide 14 from the opened position toward the active position, the resilient member 20 may be elastically deformed. It will be appreciated that depending on the configuration of the second segment 76, a gradually increasing force may be required to continuously move the ligating slide 14 along the slide track 74 toward the active position. The rate at which the force is required to increase is dictated by the shape of the central portion 70 and the properties of the resilient member 20.

With regard to the central portion 70, the second segment 76 is a generally planar surface and is believed to require a generally linear increase in force on the ligating slide 14, at least over a portion of the movement toward the active position, as shown in FIG. 3B, to deform the resilient member 20. The resilient member 20 may deform in a manner which allows it to conform to the shape defined by the distances between the region of contact between the resilient member 20 and the first segment 72 and the region of contact between the resilient member 20 and the second segment 76. Because the central portion 70 includes the segment 72, which provides a gradually decreasing clearance dimension that is less than the outside diameter of the resilient member 20, the central portion 70 interferes with movement of the resilient member 20. The ligating slide 14 therefore remains substantially in the opened position unless a force sufficient to elastically deform the resilient member 20 past the pinch point 78 is applied to the ligating slide 14.

In this regard, the resilient member 20 may elastically deform by a change in the cross-sectional profile of the member 20. This may include a change to a roughly egg-shaped cross section (not shown) in the region of contact between the resilient member 20 and the aperture 52. Portions of the resilient member 20 outside of the aperture 52 may not significantly elastically deform and thus retain their original cross-sectional profile. For example, the portions of the resilient member 20 in the bores 138, 140 may remain substantially circular. Thus, elastic deformation of the resilient member 20 may be localized to discrete regions of the resilient member 20 in sliding contact with the aperture 52. It will be appreciated that embodiments of the invention are not limited to any particular form or shape of the resilient member 20.

At some force greater than the threshold force required to initially move the ligating slide 14 towards the active position, the force applied to the ligating slide 14 is sufficient to conform the resilient member 20 to the dimension of the pinch point 78. At this magnitude of force, the resilient member 20 is elastically deformed in the region of contact with the aperture 52 so that the resilient member 20 may at least partially squeeze through the pinch point 78. The resilient member 20 may elastically deform to an egg-shaped cross section (not shown). At the pinch point 78, a leading portion of the resilient member 20 may reside within the second lobe portion 60 while a remaining portion of the resilient member 20 extends into the central portion 70. The resilient member 20 may reside partially in each of the second lobe 60 and the central portion 70. By way of example and not limitation, the force required to move ligating slide 14 to a position where the resilient member 20 partially enters the second lobe portion 60 may exceed about 0.1 kgf (kilogram force), and by way of additional example, this force may be from about 0.2 kgf to about 0.8 kgf or from about 0.5 kgf to about 0.7 kgf, preferably about 0.6 kgf.

The magnitude of the force required to overcome the threshold force and/or the threshold sliding force as the ligating slide 14 moves away from the opened position depends on the configuration of the aperture 52. This force may therefore be selectively varied by changing the configuration of the aperture 52. In this regard, relative angles of the second segment 76 and the first segment 72 may be modified to provide a desired force and/or sliding force and the rate at which that force may be increased. Furthermore, the position of the pinch point 78 may be selected to provide a shorter or longer central portion by which the rate of force increase may be changed. The shape of the first and/or second segments 72, 76 may be generally planar to provide a linearly increasing sliding force when the resilient member 20 is in the central portion 64. Alternatively, one or both of the segments 72, 76 may be contoured or curved (not shown) to provide a variable sliding force. The above-described methods for varying the opening and/or sliding force are exemplary.

Once the opening and/or sliding force meets or exceeds the force required to move the resilient member 20 to a position that is at least partially through the pinch point 78, the resilient member 20 may spontaneously slide or move the remainder of the distance into the second lobe portion 60. That is, the leading and remaining portions may spontaneously move into the second lobe portion 60 in the absence of additional external force. More specifically, once a threshold proportion of the resilient member 20 enters the second lobe portion 60, the sliding movement of the resilient member 20 into the second lobe portion 60 may proceed spontaneously. This movement may be accompanied by an audible and/or a tactile "click" or "snap" when the resilient member 20 expands into the second lobe portion 60. By this feature, the clinician may then be assured that the ligating slide 14 has reached its closed position and will remain in the closed position under normal forces observed during the orthodontic treatment.

It is believed that the elastic nature of the resilient member 20 causes a natural inclination for the resilient member 20 to return to an undeformed or at least a less deformed configuration than the deformed configuration of the resilient member 20 in the vicinity of the pinch point 78. Thus, when a threshold portion of the resilient member 20 enters the second lobe portion 60 of the aperture 52, the member 20 may spontaneously release internal elastic energy (by virtue of its deformed condition). Such a release causes the resilient member 20 in the vicinity of the pinch point 78 to move into and fill the second lobe portion 60 without application of additional external force. In other words, only a fractional portion of the resilient member 20 may enter the second lobe portion 60 when an external force is applied to the ligating slide 14 to move the ligating slide 14 to the pinch point 78. The resilient member 20 may move the remainder of the distance into the second lobe portion 60 to revert to a configuration having less or no elastic deformation.

In one embodiment, should an insufficient force be applied to the resilient member 20 so that it fails to enter the second lobe portion 60, the ligating slide 14 may move, in the absence of an external force, toward the opened position (FIG. 3A) because the resilient member 20 may gradually expand into the larger regions of the central region 70 proximate the first lobe portion 56. Ultimately, the resilient member 20 may enter the first lobe portion 56.

In one embodiment, as noted above and with reference to FIG. 3B, the third lobe portion 64 is positioned occlusally and labially relative to the second lobe portion 60. In embodiments in which the second and third lobe portions 60, 64 are generally circular, if the portions of the perimeters of the second and third lobe portions 60, 64 were extended, the perimeters would intersect at points 80 and 82. In this way, there may not be a central portion between the second and third lobe portions 60, 64. A perpendicular distance between the points 80 and 82 may be less than a diameter of one or both of the second and third lobe portions 60, 64, so as to form a pinch point 84 between the second lobe portion 60 and the third lobe portion 64. Similar to the pinch point 78, the pinch point 84 is generally a narrowing of the aperture 52 between the second and third lobe portions 60, 64. The pinch point 84 may have a dimension less than or equal to the dimension of the pinch point 78.

As set forth above, the aperture 52 may be asymmetric. In embodiments where the first and second lobe portions 56, 60 are generally circular, this asymmetry may, in part, be due to the difference in the radius dimensions R1, R2, and R3, as well as locations of the pinch points 78, 84. In embodiments in which the centers C1, C2, C3 of first, second, and third lobe portions 56, 60, 64, respectively, are positioned in three different labial-lingual planes, the varying positions may further contribute to the asymmetry. The asymmetry in the aperture 52 may produce a distinctive tactile response in the movement of the ligating slide 14. In particular, the asymmetry in the aperture 52 may provide the clinician with a distinctive "click" or "snap" to indicate each change between the opened, active, and passive positions of the ligating slide 14.

With regard to the forces required to move the slide 14, that is, the resilient member 20, from the second lobe portion 60, in which the ligating slide 14 is in the active position (FIG. 3B), to the third lobe portion 64, in which the ligating slide 14 is in the passive position (FIG. 3C), the same general principles described above with respect to the opened to active position transition apply. In this embodiment, however, elastic deformation of the resilient member 20 is affected solely by the pinch point 84, as there is no central portion intermediate the second and third lobe portions 60, 64.

With reference to FIG. 2, in the exemplary embodiment shown, the bracket body 12 includes a mesial and distal shoulder 86 extending from opposed sides of the slide support portion 48. In one embodiment, each shoulder 86 generally defines a surface that is generally parallel with the base surface 36 of the archwire slot 16. As is shown in FIG. 3B, one or more of the shoulders 86 may form a stop against which the ligating slide 14 may reside when it is in the opened position and/or the active position. The slot surface 40 extends lingually from the occlusal side of the shoulder 86. Wall 88 extends lingually from the gingival side of the shoulder 86.

With further reference to the exemplary embodiment shown in FIGS. 2 and 3B, a track surface 90 is positioned on the mesial and distal sides of the slide support portion 48. The track surface 90 generally extends between the wall 88 and the gingival side 26 of the bracket body 12. The track surface 90 has a topography configured to cooperate with the ligating slide 14 to achieve the intended function of the bracket 10.

In this regard, the track surface 90 comprises a generally planar labially-facing surface 92 having a ridge 94 and an incline or ramp 96 (shown best in FIG. 3B) positioned thereupon in spaced relation. The surface 92 is generally parallel to the base surface 36. The ridge 94 and the ramp 96 generally extend labially relative to the planar surface 92. The ridge 94 may be positioned proximate the gingival side 26 of the bracket body 12 while the ramp 96 may be positioned adjacent the wall 88. The ridge 94 includes a gingival surface 98, a labial surface 99, and an occlusal surface 100 (FIG. 3B). The gingival surface 98 is angled or sloped so as to effectively operate as a camming surface for the ligating slide 14. The labial surface 99, which is positioned intermediate the gingival surface 98 and the occlusal surface 100, may be generally parallel to the base surface 36. The occlusal surface 100 may descend from the labial surface 99 to the planar surface 92 at a sharp angle generally perpendicular to the planar surface 92. The ramp 96 may comprise an angled surface 97 of track surface 90 extending between the generally planar surface 92 and the wall 88. The ramp 96 may have a same angle relative to the planar surface 92 as the gingival surface 98 of the ridge 94. The ramp 96 may have a small shelf 102 comprising a generally planar surface at the labial-most position on the ramp 96, adjacent the wall 88. The shelf 102 may be generally parallel to the base surface 36. The shelf 102 and the labial surface 99 may be positioned at a same height above the planar surface 92.

In another aspect of the exemplary embodiment shown, and as best shown in FIG. 3B, a cutout 106 may be formed in the labial side 32 of the bracket body 12 adjacent slot surface 38, and the cutout 106 may define a labially-facing ledge 108 that lies in a plane that is positioned labially of a plane in which the shoulders 86 lie. The cutout 106 further defines an occlusal surface 110 generally perpendicular to the ledge 108. The ledge 108 is configured to engage the ligating slide 14 in the passive ligating position. In this way, when the ligating slide 14 is in the passive position, the archwire slot 16 effectively has a greater lingual-labial dimension than when the ligating slide 14 is in the active position. This will be discussed in greater detail below.

With reference to FIG. 2, the ligating slide 14 is generally a U-shaped configuration. When mounted to the labial surface of the tooth T carried on the patient's lower jaw, the ligating slide 14 has a lingual side 120, an occlusal side 122, a gingival side 124, a mesial side 126, a distal side 128, and a labial side 130. The ligating slide 14 includes a first leg or mesial portion 132 and second leg or a distal portion 134 that generally define a slide channel 136 therebetween. The slide channel 136 is dimensioned to slidably cooperate with the slide support portion 48 on the bracket body 12. In one embodiment, the slide channel 136 has a uniform shape and width that generally corresponds to the shape and width of the slide support portion 48 of the bracket body 12 such that the slide support portion 48 may be received in the slide channel 136.

Figure 4:
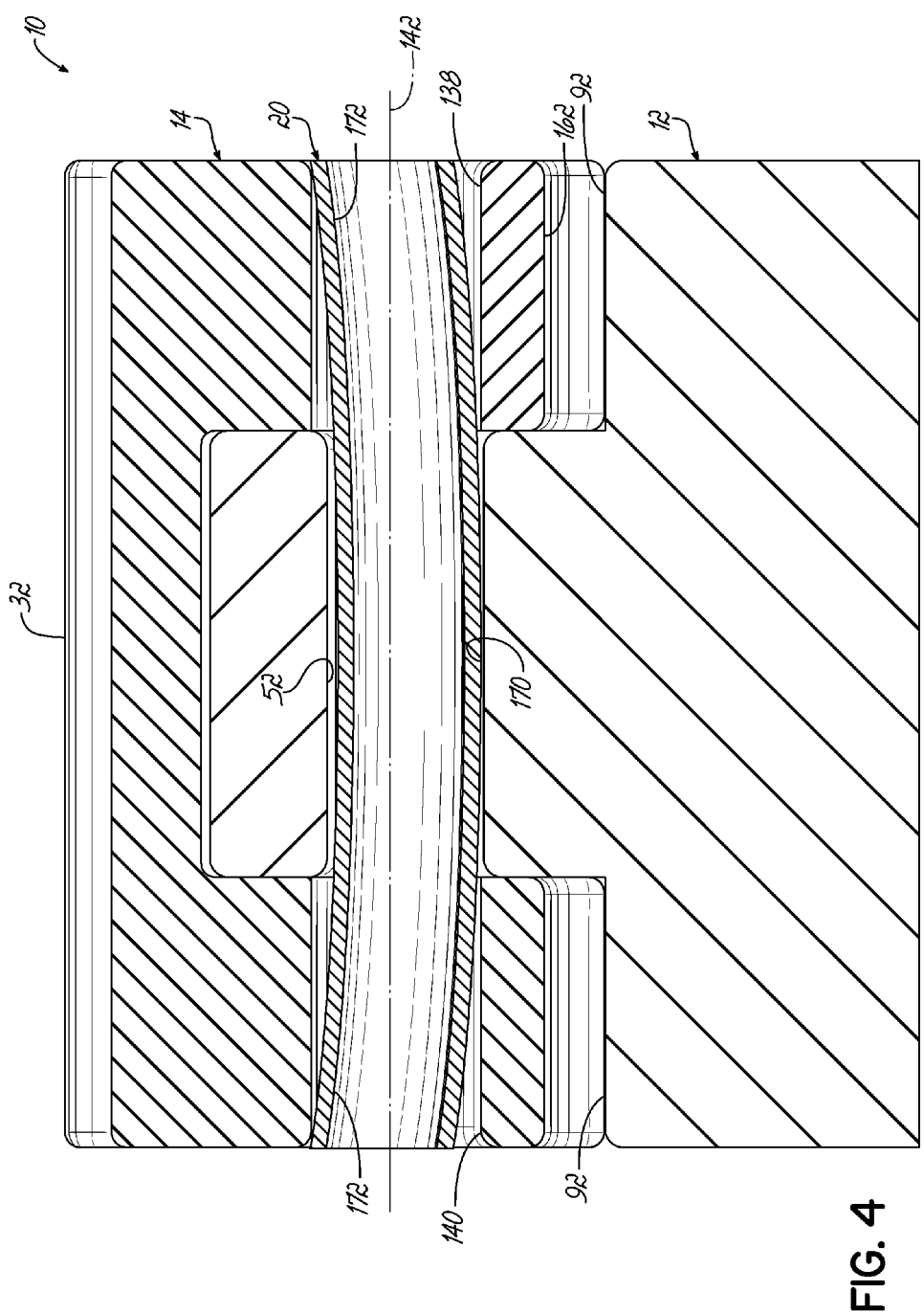
FIG. 4 is a cross-sectional view of the orthodontic bracket taken along section line 4-4 of FIG. 1.
Figure 5:
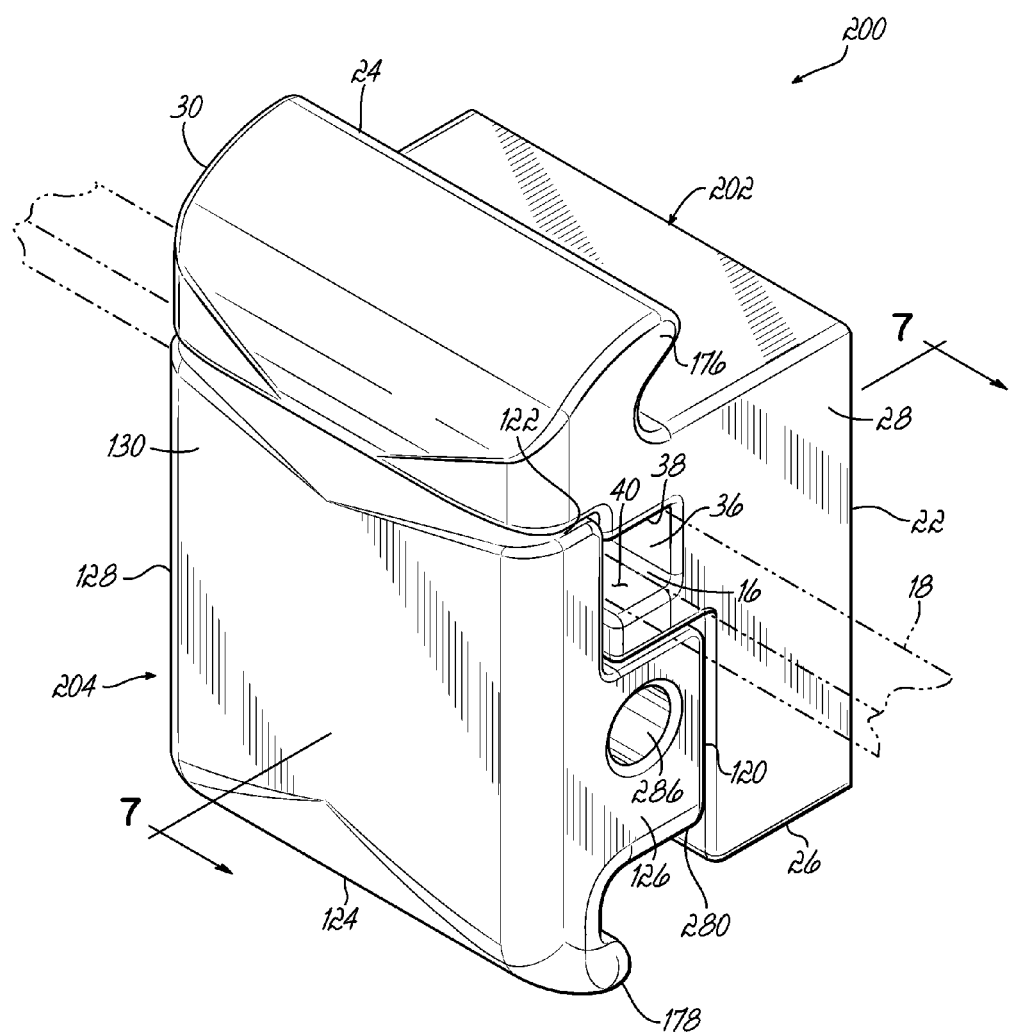
FIG. 5 is a perspective view of an orthodontic bracket according to another embodiment of the invention, a slide member shown in the active position.

With continued reference to FIG. 2, each of the mesial and distal portions 132, 134 includes at least one through-bore that receives a portion of the resilient member 20. As shown, the mesial portion 132 includes a mesial through-bore 138 and the distal portion 134 includes a distal through-bore 140. The bores 138, 140 share a common axis 142. As shown in FIG. 4, the resilient member 20 is positioned in the bore 138 and through the aperture 52 and into the opposing bore 140 along axis 142. Thus, the resilient member 20 when coupled to the ligating slide 14 moves with the ligating slide 14 and extends through and moves relative to the aperture 52. By this construction, the resilient member 20 may provide a mechanism for securing or retaining the ligating slide 14 to the bracket body 12 in the opened, active, and/or passive positions.

In one embodiment and with reference to FIG. 3A, the resilient member 20 cooperates with the bracket body 12, and more particularly to first, second, and third lobe portions 56, 60, 64 of the aperture 52, to secure the ligating slide 14 to the bracket body 12 in respective opened, active, and passive positions. It will be appreciated that the bore 138 and the bore 140 may be sized to be slightly larger than the diameter or equivalent dimension of the resilient member 20. By way of example, the bores 138, 140 may be about 0.002 inch larger in dimension than the largest corresponding outer dimension of the resilient member 20. By way of further example, the bores 138, 140 may measure from about 10% to about 20% larger than the corresponding outer dimension of the resilient member 20. The resilient member 20 may be dimensioned to fit within the bores 138, 140 and through the aperture 52. During assembly, the resilient member 20 may be press fit or slip fit into bores 138, 140, and/or may be secured therein to prevent relative movement therebetween using various processes including staking, tack welding, laser welding, adhesives, or other suitable methods.

In one embodiment and with continued reference to FIG. 2, lingual edges of the mesial and distal portions 132, 134 each comprise a ligating surface 146 adjacent the occlusal side 122 of the ligating slide 14 and a track surface 148 proximate the gingival side 124 of the ligating slide 14, the track surface 148 being lingual the ligating surface 146. An intermediate wall 150 may connect the ligating surface 146 and the track surface 148.

In one embodiment shown in FIGS. 2 and 3B, the ligating surfaces 146 are planar and are configured to slidingly engage with the shoulders 86 and/or the ledge 106 during at least a portion of the movement of the ligating slide 14 between the various positions. Portions of each of the ligating surfaces 146 may oppose the base surface 36 when the ligating slide 14 is in the active and passive positions, and thereby effectively form a fourth side of the archwire slot 16. In this regard, in the embodiment shown in FIG. 3B, the ligating surfaces 146 form the labial boundary of the archwire slot 16 to capture the archwire 18 (FIG. 1) in the archwire slot 16 during orthodontic treatment.

In addition, in one embodiment, the ligating surfaces 146 are configured to abut the mesial and distal shoulders 86 when the ligating slide 14 is in the opened and active positions as is shown in FIGS. 3A and 3B, respectively. As introduced above, the resilient member 20 may bias the ligating slide 14 in a direction generally perpendicular to the direction of translational motion of the ligating slide 14. This may include a direction that is toward the base surface 36 of the archwire slot 16.

As is shown in FIG. 3B, in one embodiment, when the ligating slide 14 is in the active position, the ligating surfaces 146 may not extend the full height (i.e., from the slot surface 38 to the slot surface 40) of the archwire slot 16. In this regard, mesial and distal portions 132, 134 further include generally occlusally oriented leading surfaces 152. In the embodiment shown, the leading surfaces 152 do not contact the opposing slot surface 38. Accordingly, there remains a gap 154 between the slot surface 38 and the ligating slide 14 when in the active ligation position.

Similarly, in one embodiment, when the ligating slide 14 is in the passive position, as is shown in FIG. 3C, the occlusally oriented leading surfaces 152 do not extend to the occlusal surface 110 of the cutout 106. Accordingly, there remains a gap 156 between the occlusal surface 110 and the ligating slide 14 at this location. The gap 156 may be sized to receive a tool for forcing the ligating slide 14 to the opened position from either of the passive or active positions.

According to an exemplary embodiment shown in FIG. 3B, the wall 150 has a height equal to the distance between the generally planar portion 92 of the track surface 90 and the shoulder 86. When the ligating slide 14 is in the opened and active positions (FIGS. 3A and 3B, respectively), a top of the wall 150 is positioned generally coplanar with the shoulder 86. When the ligating slide 14 is in the passive position (FIG. 3C), the wall 150 extends above the shoulder 86 a distance equivalent to a height between the generally planar surface 92 and a labial-most point on the ramp 96 of the track surface 90. When the ligating slide 14 is the opened position (FIG. 3A), the wall 150 is spaced a first distance from the wall 88. When the ligating slide 14 is in the active position (FIG. 3B), the wall 150 is spaced a second distance shorter than the first distance from the wall 88. When the ligating slide 14 is the passive position (FIG. 3C), the wall 150 abuts the wall 88.

With continued reference to FIGS. 2 and 3A-3C, in one embodiment, the track surface 148 of the ligating slide 14 is configured to cooperate with the track surface 90 of the bracket body 12. In the exemplary embodiment shown in FIG. 2, the track surface 148 has a leading edge 160 at an intersection with the wall 150 (i.e., at an occlusal end of the track surface 148). A recess 162 is positioned in the track surface 148 proximate the leading edge 160. The recess 162 has an occlusal wall 164 and a gingival wall 166. The gingival wall 166 effectively operates as another cam against the track surface 90.

With further reference to the exemplary embodiment of FIG. 3A, in the opened position, the leading edge 160 of the slide track surface 148 is positioned occlusally of the ridge 94 of the bracket body 12. The ridge 94 is positioned within the recess 162, such that the occlusal side 100 of the ridge 94 at least partially contacts the occlusal wall 164 of the recess 162. The gingival wall 166 of the recess 162 extends beyond or overhangs the gingival side 26 of the bracket body 12. The common axis 142 of each of the bores 138, 140 may be aligned with the axis 58 of the first lobe portion 56. The axis 1 of the resilient member 20 may also be aligned with the axis 58 depending on the cross-sectional dimensions of the resilient member 20. Generally, in this position, and where each of the first lobe portion 56 and bores 138, 140 is generally larger in dimension than the resilient member 20, the resilient member 20 is in a relaxed, undeformed state and may not bias the ligating slide 14 in any given direction. Where the bracket 10 is mounted on the labial surface of a lower tooth, gravity, as well as an interaction between the occlusal wall 164 of the recess 162 and the ridge 94, will tend to maintain the ligating slide 14 in the opened position.

With reference to the exemplary embodiment of FIGS. 3B and 4, in which the ligating slide 14 is shown in the active position, the leading edge 160 is positioned on the ramp 96 intermediate the generally planar surface 92 and the shelf 102, the ridge 94 is positioned in the recess 162, and the gingival wall 166 of the recess 162 is positioned adjacent to or at least partially abuts the gingival side 98 of the ridge 94. In the active position, the resilient member 20 is positioned in the second lobe portion 60. At least a portion of the second lobe portion 60 may reside lingually of the mesial and distal bores 138, 140, such that the second lobe portion 60 and the bores 138, 140 are not fully aligned. As such, and as shown in FIG. 4, a center portion 170 of the resilient member 20 is positioned lingually relative to end portions 172 thereof. As such, the axis 1 of the resilient member 20 is curved lingually, and the resilient member 20 imposes a biasing force on the ligating slide 14 generally in the lingual direction. More specifically, the resilient member 20 may bias the ligating slide 14 toward the shoulder 86 and the base surface 36 of the bracket body 12, which helps to actively ligate the archwire 18 in the archwire slot 16 (i.e., when the archwire 18 substantially fills the archwire slot 16). Accordingly, the resilient member 20 provides more consistent contact between the ligating slide 14 and the bracket body 12.

With reference to FIGS. 2 and 3B, as described above, in the active position, the ligating surfaces 146 of ligating slide 14 are cantilevered to extend at least partially over the archwire slot 16. The ligating surfaces 146 extend sufficiently far over the archwire slot 16 so as to prevent removal of the archwire 18 therefrom. In this way, the ligating surfaces 146 effectively operate as a fourth side of the archwire slot 16. The depth of the archwire slot 16 in the generally labial-lingual direction is determined by the position of the shoulders 86 relative to the base surface 36 of the archwire slot 16. The biasing force of the resilient member 20 provides a relatively consistent contact between the ligating surfaces 146 and the shoulders 86. In one embodiment, the archwire slot 16 may have a depth of approximately 0.018 inch to approximately 0.028 inch. It will be appreciated that for the bracket 10 to actively ligate the archwire 18, the archwire 18 must have a diameter or other dimension that is greater than the depth of the archwire slot 16 when the ligating slide 14 is in the active position, as is shown in FIG. 3B. For example, the bracket 10 may be active for an archwire having a 0.020 inch dimension when the ligating slide 14 is in the active position. In this representative example, the wall 88 is less than about 0.020 inch. However, it will be appreciated that archwires smaller than 0.020 inch may be actively ligated. For example, where the wall 88 is less than 0.016 inch, a 0.016 inch archwire may be actively ligated. Thus, the dimensions of the bracket body 12, for example, the height of the wall 88, may be adjusted to ligate smaller archwires according to the principles disclosed herein.

With continued reference to the exemplary embodiment shown in FIGS. 3A and 3B, and as will be described further below, in order for the ligating slide 14 to pass from the opened position to the active position (and for the leading edge 160 to partially ascend the ramp 96), a sufficient force must be applied to the ligating slide 14 to pass the resilient member 20 through the pinch point 78 between the first and second lobe portions 56, 60 of the aperture 52. A similar force is likewise required to move the ligating slide 14 in the opposite direction, from the active position (FIG. 3B) to the opened position (FIG. 3A).

With reference to the exemplary embodiment of FIGS. 2 and 3C, when the ligating slide 14 is in the passive position, the leading edge 160 is supported on the shelf 102 (adjacent the wall 88), the gingival wall 166 of the recess 162 is supported on the ridge 94, and an entire length of the track surface 148 at the recess 162 is spaced from the track 90. In the passive position, the resilient member 20 is positioned in the third lobe portion 64. The third lobe portion 64 may be aligned with the mesial and distal bores 138, 140 (labeled in FIG. 2), or at least a portion of the third lobe portion 64 may reside lingually of the bores 138, 140. In an embodiment in which at least a portion of the third lobe portion 64 resides lingually of the bores 138, 140, there may be better alignment between the third lobe portion 64 and the bores 138, 140 than between the second lobe portion 60 and the bores 138, 140. Nonetheless, the center portion 170 of the resilient member 20 may be positioned slightly lingually relative to the end portions 172 thereof. As such, the axis 1 of the resilient member 20 may be slightly curved lingually (as is shown in FIG. 4), and the resilient member 20 may impose a biasing force on the ligating slide 14 generally in the lingual direction.

The resilient member 20 slightly biases the ligating slide 14 toward the ledge 108 and the bracket base 36. As mentioned above, in the passive position, the ligating surfaces 146 of the ligating slide 14 effectively operate as a fourth side to the archwire slot 16. In the passive position, the ligating slide 14 inhibits removal of the archwire 18 from the archwire slot 16 without substantially inhibiting movement therein (i.e. when the archwire 18 is smaller than the archwire slot 16). In one embodiment, the archwire slot 16 may have a depth of approximately 0.020-0.027 inch. More specifically, in one embodiment, the archwire slot 16 may have a depth of approximately 0.027 inch. In order for this embodiment to passively ligate the archwire 18, the archwire 18 must have a diameter or other dimension of less than 0.027 inch. If the diameter of the archwire 18 is greater than 0.027 inch, the archwire 18 may experience active ligation.

With continued reference to FIGS. 3B and 3C, in order for the ligating slide 14 to pass from the active position (FIG. 3B) to the passive position (FIG. 3C) (and for the leading edge 160 and the gingival edge 166 to ascend the respective shelf 102 and ridge 94), a sufficient force must be applied to the ligating slide 14 to pass the resilient member 20 through the pinch point 84 between the second and third lobe portions 60, 64 of the aperture 52. A similar force is likewise required to move the ligating slide 14 in the opposite direction, that is, from the passive position (FIG. 3C) to the active position (FIG. 3B).

Additionally, in one embodiment, and with reference to FIG. 1, the bracket body 12 may include an occlusal tie wing 176. The ligating slide 14 may also include a gingival tie wing 178. It will be appreciated that the opposing tie wings 176, 178 may provide a region in which the clinician may engage a ligature, for example, to provide additional pressure on the ligating slide 14 to maintain it against the bracket body 12 and in the active or passive positions during treatment.

With reference now to an embodiment of the present invention shown in FIGS. 5-7C, an orthodontic bracket 200 is described. The same description and reference numerals used to describe the embodiment of the bracket 10 shown in FIGS. 1-4 apply to bracket 200 unless indicated otherwise. Unlike the bracket 10, which converts from the opened position to the active position to the passive position, the orthodontic bracket 200 converts from an opened position to a passive position to an active position. The bracket 200 includes a bracket body 202 and a ligating slide 204 slidably coupled with the bracket body 202.

Figure 6:
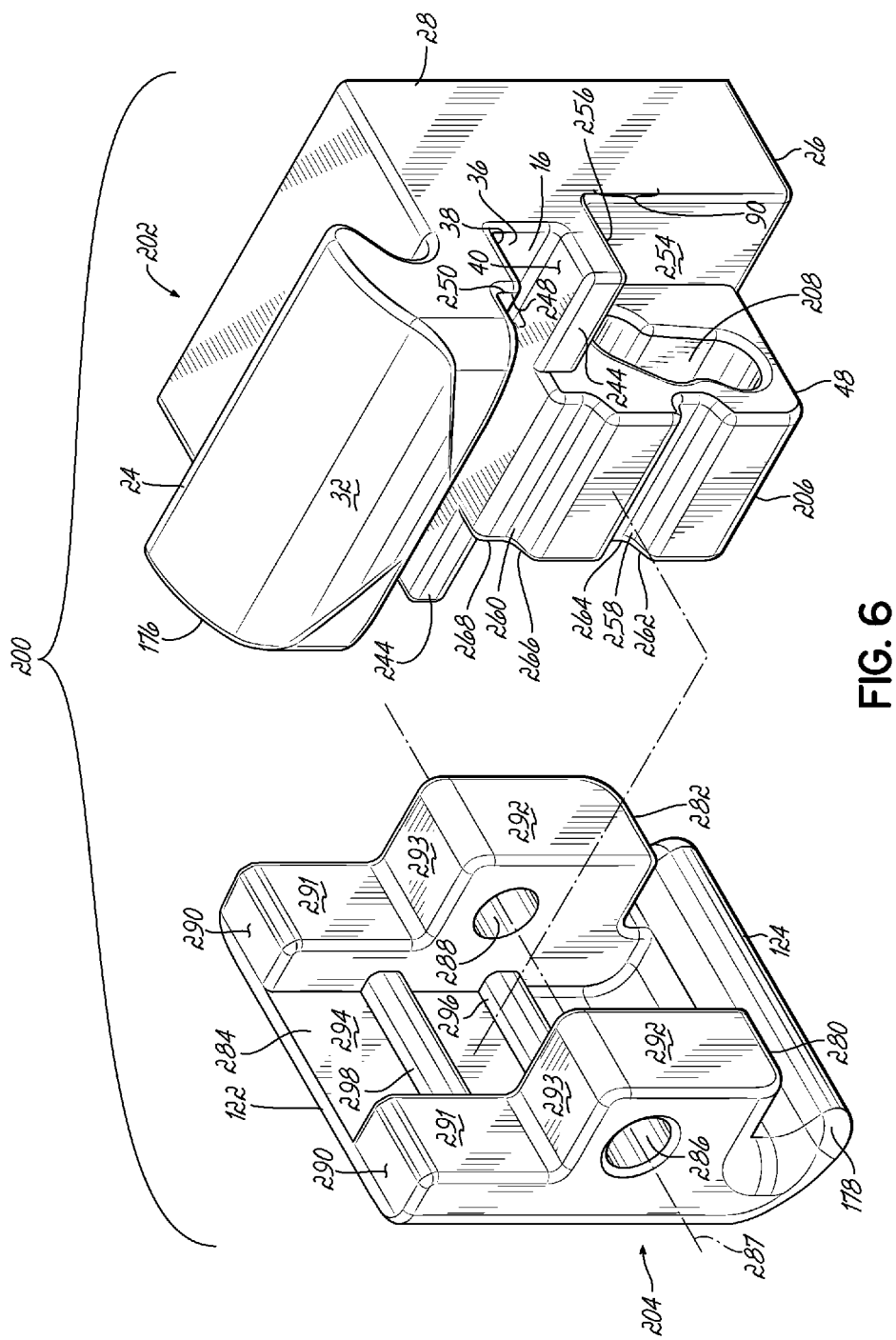
FIG. 6 is an exploded perspective view of the orthodontic bracket shown in FIG. 5.

With reference to FIG. 6, the bracket body 202 includes a slide support portion 206 configured to receive the ligating slide 204 thereon. The slide support portion 206 includes an aperture 208 formed as a through-bore in the mesial-distal direction. Similar to the aperture 52 in the bracket 10, in one embodiment, the aperture 208 is a generally asymmetrical bore that may be described as having an irregular configuration.

Figure 7A:
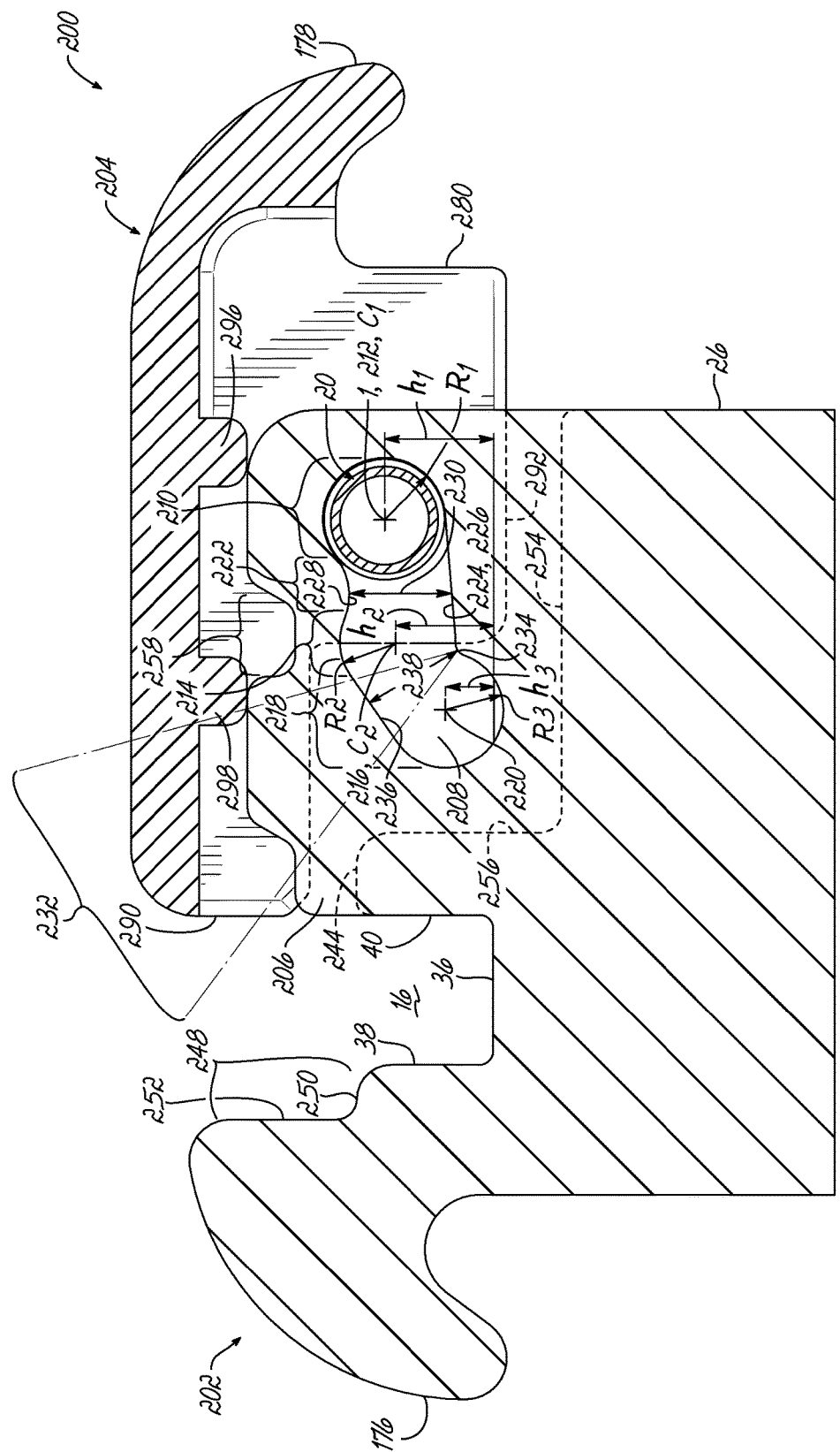
FIG. 7A is a cross-sectional view of the orthodontic bracket taken along section line 7-7 of FIG. 5, depicting the slide member in the opened position.
Figure 7B:
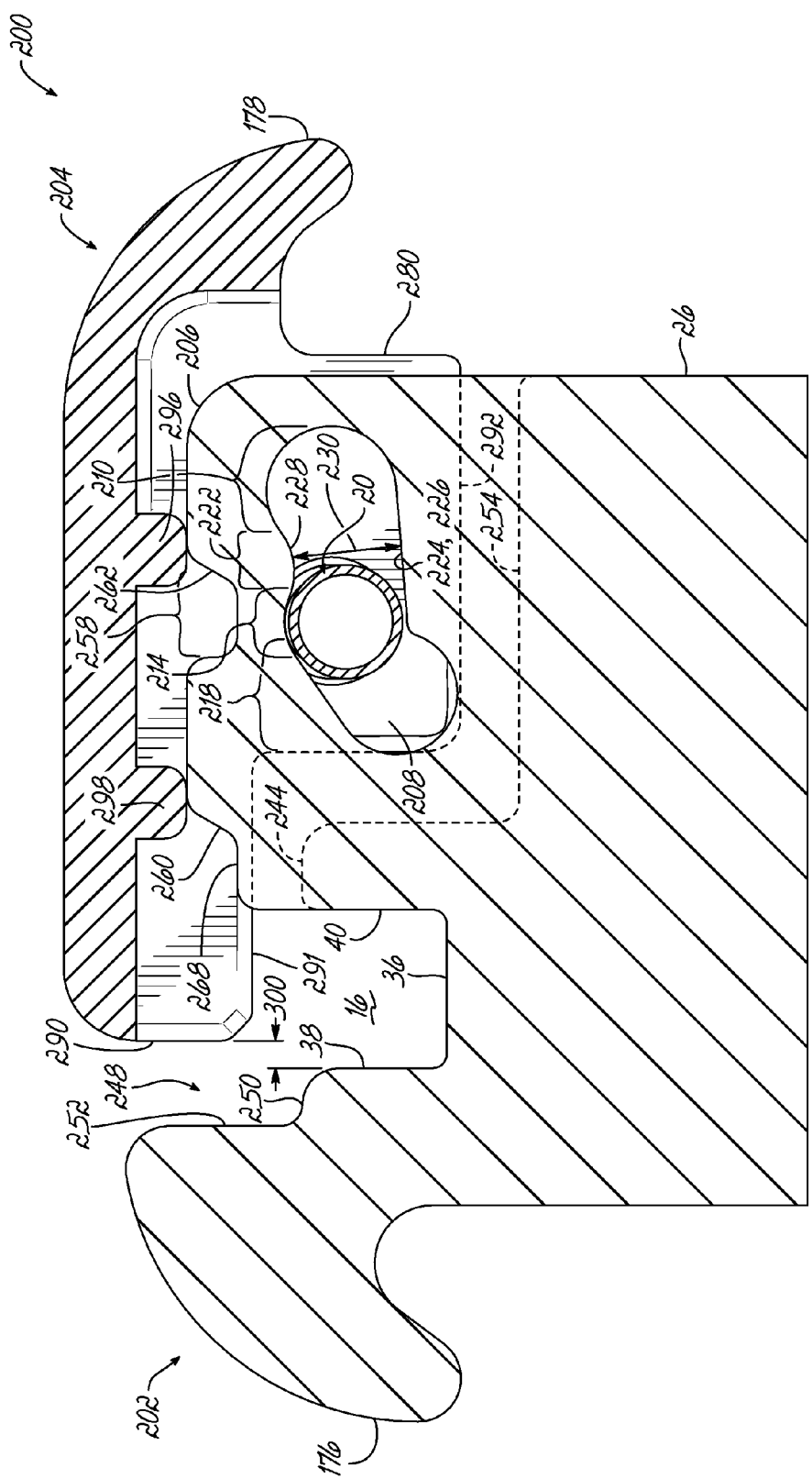
FIG. 7B is a cross-sectional view of the orthodontic bracket taken along section line 7-7 of FIG. 5, depicting the slide member in the passive position.
Figure 7C:
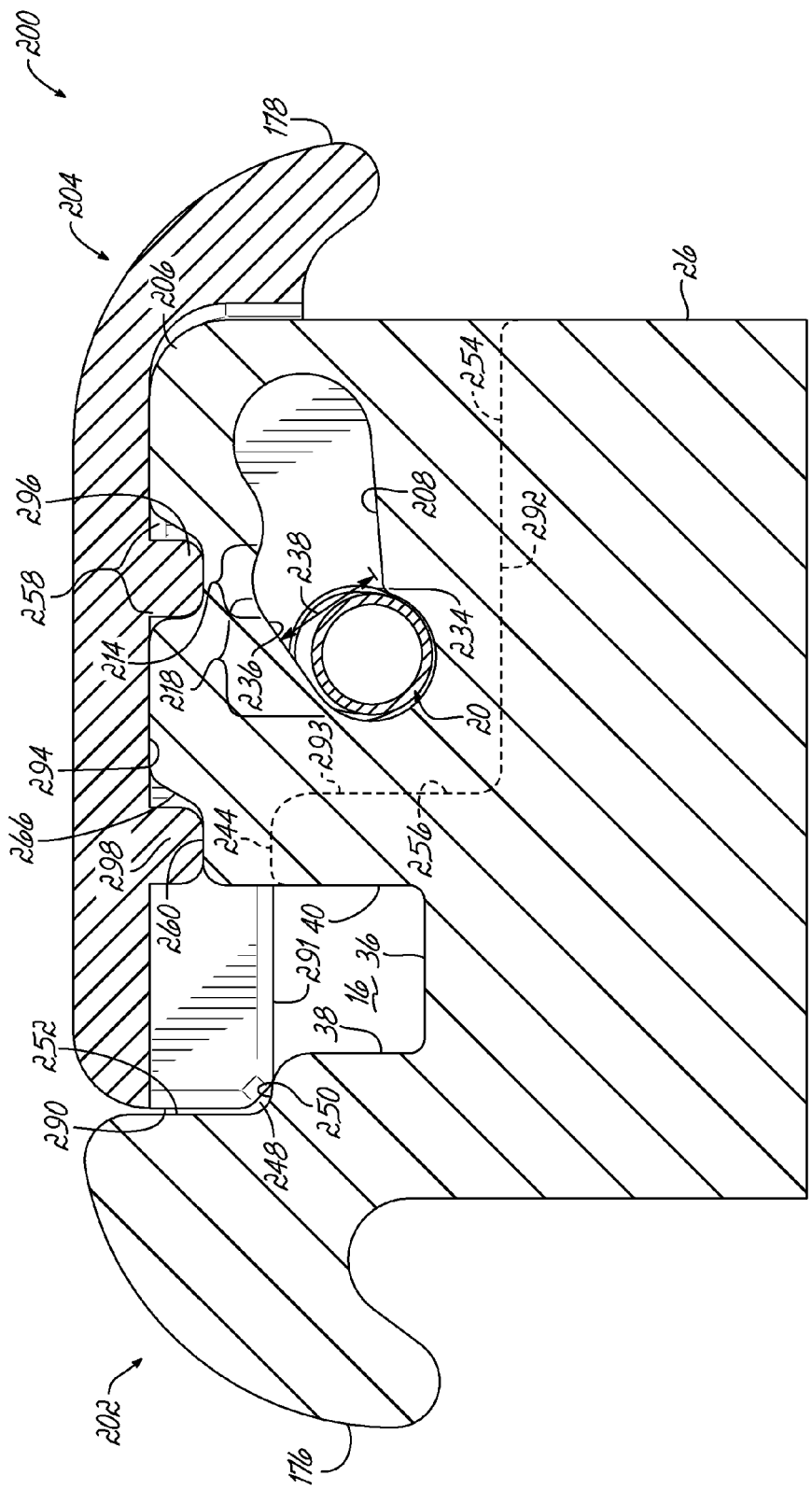
FIG. 7C is a cross-sectional view of the orthodontic bracket taken along section line 7-7 of FIG. 5, depicting the slide member in the active position.

As shown in FIGS. 7A-7C, the aperture 208 may include a first lobe portion 210 proximate the gingival side 26. By way of example only, the first lobe portion 210 may define a generally circular perimeter along a portion of the aperture 208. The lobe portion 210 may be defined by an axis 212 and a radius R1. The lobe portion 210 may have a center C1 located a height h1 relative to the base surface 36 of the bracket body 202. The aperture 208 may further include a second lobe portion 214 positioned occlusally relative to the first lobe portion 210. Similar to the first lobe portion 210, the second lobe portion 214 may be defined by a generally circular perimeter having axis 216 and a radius R2. The second lobe portion 214 may have a center C2 located at a height h2 relative to the base surface 36 of the bracket body 202, where h1 is not equal to h2. In one embodiment, the height h2 is slightly less than height h1. Thus, the second lobe portion 214 is positioned slightly lingually of the first lobe portion 210. The aperture 208 may still further include a third lobe portion 218 positioned occlusally relative to the second lobe portion 214, such that the lobe portion 218 is proximate the archwire slot 16. Similar to the first and second lobe portions 210, 214, the third lobe portion 218 may be defined by a generally circular perimeter having axis 220 and radius R3. The third lobe portion 220 may have a center C3 located at a height h3 relative to the base surface 36 of the bracket body 202, where h3 is not equal to either of h1 or h2. In one embodiment, the height h3 may be less than both h1 and h2. Thus, the third lobe portion 218 is positioned slightly lingually of the second lobe portion 214.

In one embodiment, the aperture 208 may include a central portion 222 positioned between and connecting the first lobe portion 210 and the second lobe portion 214. The central portion 222 may include a first segment 224. The first segment 224 may be tangent to the first lobe portion 210, but may extend in a direction such that an extension of the first segment 224 would intersect (rather than be tangent to) the second lobe portion 214. The first lobe portion 210, the second lobe portion 214, and the first segment 224 may generally define a portion of a slide track 226. In addition, the central portion 222 may include a second segment 228 opposite the first segment 224. The second segment 228 may comprise an arcuate curve running between the first lobe portion 210 and the second lobe portion 214.

In one embodiment, the orientation of the first segment 224 and the second segment 228 of the central portion 222 forms a restriction or pinch point 230 between the first lobe portion 210 and the second lobe portion 214. Dimensions of the pinch point 230 may be similar to those described above with respect to aperture 52 of the orthodontic bracket 10. Generally, the smallest dimension of the pinch point 230 is less than the diameter of the resilient member 20.

In one embodiment, the aperture 208 may further include a central portion 232 positioned between and connecting the second lobe portion 214 and the third lobe portion 218. The central portion 232 may merely comprise a point 234 on the lingual portion of the slide track 226 at a point where the second and third lobe portions 214, 218 would intersect if they had complete perimeters. The central portion 232 may also include a segment 236 that is tangent to the second lobe portion 214 and the third lobe portion 218.

In one embodiment, the orientation of the point 234 and the segment 236 of the central portion 232 forms a restriction or pinch point 238 between the second lobe portion 214 and the third lobe portion 218. Dimensions of the pinch point 238 may be similar to those described above with respect to aperture 52 of the orthodontic bracket 10.

With reference to FIGS. 6-7A, and as described above with respect to the bracket 10, the bracket body 202 includes mesial and distal shoulders 244. The bracket body 202 may further include a cutout 248 that may be formed in the labial side 32 of the bracket body 202 adjacent the slot surface 38, and the cutout 248 may define a ledge 250. Unlike the embodiment described above, the ledge 250 may be in a same plane as the shoulders 244. The cutout 248 may further define an occlusal surface 252 generally perpendicular to the ledge 250. Both the shoulders 244 and the ledge 250 are configured to engage the ligating slide 202 in the active position, as is shown in FIG. 7C.

With further reference to FIGS. 6-7C, a surface 254 is positioned on each mesial and distal side of the slide support portion 206. The surface 254 may be generally planar so as to correspond with a generally planar lingual edge of the ligating slide 204. Unlike the embodiment described above, the surface 254 may not effect a lingual-labial position of the ligating slide 204. On each mesial and distal side of the slide support portion 206, a wall 256 also extends lingually from the gingival side of the shoulder 244.

In one embodiment, a topography of the slide support portion 206 may be configured to cooperate with the ligating slide 204 so as to effect a lingual-labial position thereof. In an exemplary embodiment shown in FIGS. 6-7C, the slide support portion 206 may include two grooves positioned therein. A first groove 258 is positioned substantially labial the second lobe portion 214. A second groove 260 is positioned in spaced relation to the first groove 258 substantially labially of the shoulder 244. The first groove 258 has a gingival wall 262 leading to a base 264 of the groove 258. The gingival wall 262 is angled so as to effectively operate as a camming surface for a camming member of the ligating slide 204, as described in detail below. The second groove 260 also has a gingival wall 266 and a base 268, similar to the respective wall 262 and base 264.

With reference to FIG. 6, the ligating slide 204 is generally a U-shaped configuration. The ligating slide 204 includes a first leg or mesial portion 280 and second leg or a distal portion 282 that generally define a slide channel 284 therebetween. The mesial portion 280 includes a mesial through bore 286, and the distal portion 282 includes a distal through bore 288 having a common axis 287 and the same relative configurations as described above with respect to the bracket 10. The slide channel 284 is dimensioned to slidably cooperate with the slide support portion 206. In one embodiment, the slide channel 284 has a uniform width that generally corresponds to the shape of the slide support portion 206 of the bracket body 202.

With continued reference to FIG. 6, in one embodiment, the mesial and distal portions 280, 282 each have a generally occlusally oriented leading surface 290 configured to contact the occlusal surface 252 of the cutout 248. Lingual edges of the mesial and distal portions 280, 282 each comprise a surface 291 adjacent the occlusal side 122 of the ligating slide 204, and a surface 292 proximate the gingival side 124 of the ligating slide 204 and positioned lingually relative to the surface 291. The surfaces 291 are configured to contact the shoulders 244 and/or the ledge 250. The surfaces 292 are configured to contact the surfaces 254 of the bracket body 202, and in one embodiment, the surfaces 292 are generally planar. A labial-lingual wall 293 may connect the surface 291 and the surface 292. The wall 293 is configured to contact the wall 256.

In one embodiment, the slide channel 284 is defined by a labial surface 294 (i.e., a lingual surface of the ligating slide 204) that is configured to contact and slide against the slide support surface 206. The surface 294 includes a first protrusion 296 generally corresponding in shape and size to the groove 258 in the slide support surface 206 and a second protrusion 298 generally corresponding in shape and size to the groove 260. The protrusions 296, 298 are configured to effectively operate as camming members that cooperate with the gingival walls 262, 266 of the first and second grooves 258, 260. A distance between the protrusions 296, 298 may be generally equal to a distance between the gingival walls 262, 266 of the grooves 258, 260.

With reference to the exemplary embodiment of FIG. 7A, in the opened position, the protrusion 296 is supported on the slide support surface 206 proximate the gingival side 26 of the bracket body 202. The protrusion 298 is supported on the slide support surface 206 occlusally of the groove 258. The common axis 287 (FIG. 6) of each of the bores 286, 288 may be aligned with the axis 212 of the first lobe portion 210. The axis 1 of the resilient member 20 may also be aligned with the axis 212 depending on the cross-sectional dimensions of the resilient member 20. Generally, in this position, and where each of the first lobe portion 210 and bores 286, 288 is generally larger in dimension than the resilient member 20, the resilient member 20 is in a relaxed, undeformed state and may not bias the ligating slide 204 in any given direction. In the opened position, the ligating slide 204 may not contact the surface 254 or the shoulders 244 of the bracket body 202. Where the bracket 10 is mounted on the labial surface of a lower tooth, gravity will tend to maintain the ligating slide 204 in the opened position.

With reference to the exemplary embodiment of FIG. 7B, in the passive position, the protrusion 296 is supported on the slide support surface 206 at least partially gingivally of the groove 258, and the protrusion 298 is supported at least partially gingivally of the groove 260. In one embodiment, the protrusions 296, 298 may be positioned at least partially labial the grooves 258, 260, so as to partially overhang the walls 262, 266, as shown. In the passive position, the resilient member 20 is positioned in the second lobe portion 214. The second lobe portion 214 may be aligned with the mesial and distal bores 286, 288, or at least a portion of the second lobe portion 218 may reside lingual the bores 286, 288 (FIG. 6).

In the embodiment in which at least a portion of the second lobe portion 218 resides linguallly of the bores 138, 140 (FIG. 6), the center portion 170 of the resilient member 20 may be positioned slightly linguallly relative to the end portions 172 thereof. As such, the axis 1 of the resilient member 20 may be slightly curved lingually, and the resilient member 20 may impose a biasing force on the ligating slide 204. As such, the resilient member 20 slightly biases the ligating slide 204 toward the base surface 36.

In the passive position, as is shown in FIG. 7B, the surfaces 291 at least partially extend over the archwire slot 16 so as to prevent removal of the archwire 18 therefrom. A gap 300 may be present between the occlusally leading surface 290 and the slot surface 38. Nonetheless, the surfaces 291 may effectively operate as a fourth side of the archwire slot 16. In the passive position, the ligating slide 204 inhibits removal of the archwire 18 from the archwire slot 16 without substantially inhibiting movement therein, so long as the archwire 18 does not substantially fill the extended archwire slot 16.

With continued reference to FIG. 7B, in order for the ligating slide 204 to pass from the opened position (FIG. 7A) to the passive position (FIG. 7B) (and for the protrusion 298 to pass over the groove 260), a sufficient force must be applied to the ligating slide 204 to pass the resilient member 20 through the pinch point 230 between the first and second lobe portions 210, 214 of the aperture 208. A substantially equal force is required to pass from the passive position back to the opened position. In the passive position, the ligating slide 204 may not contact the surface 254 or the shoulder 244 of the bracket body 202.

With reference to the exemplary embodiment of FIG. 7C, in the active position, the protrusion 296 is positioned in the groove 258, and the protrusion 298 is positioned in the groove 260. In this embodiment, because a height of the protrusions is substantially equal to a depth of the grooves, almost the entire surface 294 of the slide channel 284 is in contact with the slide support portion 206 of the bracket body 202. In the active position, the resilient member 20 is positioned in the third lobe portion 218, as shown. At least a portion of the third lobe portion 218 may reside lingually of the mesial and distal bores 286, 288, such that the third lobe portion 218 and the bores 286, 288 are not fully aligned. The relative misalignment between the bores 286, 288 and the third lobe portion 218 requires the resilient member 20 to bend slightly, as is described below.

With continued reference to FIG. 7C, in order for the ligating slide 204 to pass from the passive position (FIG. 7B) to the active position (FIG. 7C), a sufficient force must be applied to the ligating slide 204 to pass the resilient member 20 through the pinch point 238 between the second and third lobe portions 214, 218 of the aperture 208. In the active position, an entire length of the lingual surface 292 and the wall 293 of the ligating slide 204 may contact the bracket body 202. In another embodiment, the occlusally leading surfaces 290 of the ligating slide 204 may contact the occlusal surface 252 of the cutout 248.

When the ligating slide 204 is in the active position, shown in FIG. 7C, the center portion 170 (FIG. 4) of the resilient member 20, which generally includes at least a portion of the resilient member 20 within the aperture 208 is positioned lingually relative to end portions 172 thereof. Although not shown, the axis 1 of the resilient member 20 is curved lingually, and the resilient member 20 imposes a biasing force on the ligating slide 204. More specifically, the resilient member 20 may bias the ligating slide 204 toward the shoulders 244, the ledge 250, and the base surface 36 of the bracket body 202, which helps to actively ligate the archwire 18 in the archwire slot 16 (i.e. when the archwire 18 substantially fills the archwire slot 16). Accordingly, the resilient member 20 provides more consistent contact between the ligating slide 204 and the bracket body 202. For example, the bias may provide more consistent contact between the surfaces 291 with the shoulders 244 and the ledge 250. The depth of the archwire slot 16 is equal to the height of the shoulders 244 and the ledge 250. Due to the biasing of the ligating slide 204 against the shoulders 244 and the ledge 250, other tolerance variations may no longer have a bearing on the close fit between the archwire slot 16 and the archwire 18.

Figure 8:
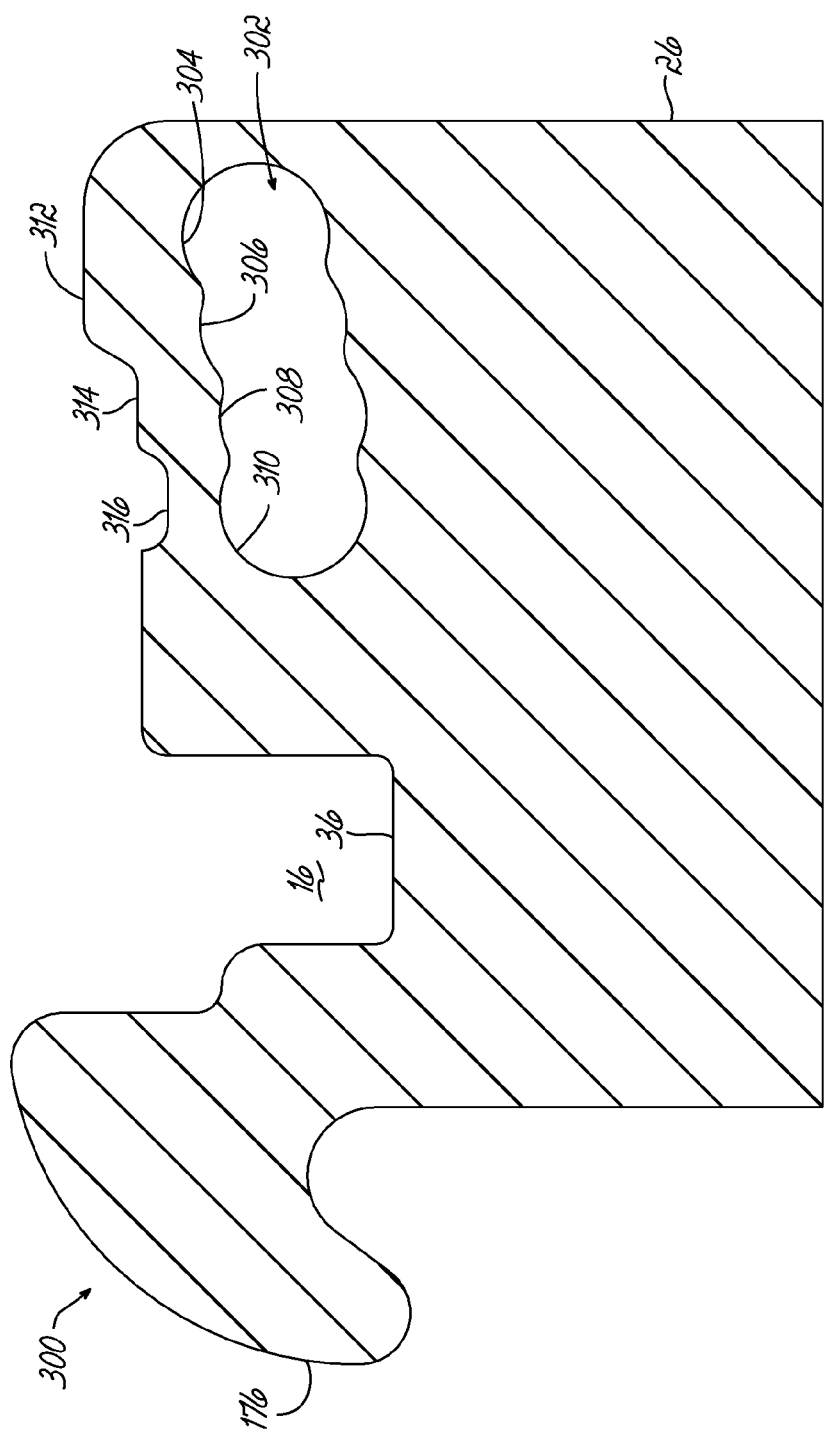
FIG. 8 is a side elevation view of a bracket body according to one embodiment of the present invention.

In another embodiment, and with reference to FIG. 8, the bracket body 300 may include the aperture 302 having more than three lobe portions as described above. In this case, the clinician may move the ligating slide (not shown) from a first lobe portion 304 to a second lobe portion 306 to a third lobe portion 308 to a fourth lobe portion 310. Corresponding step positions 312, 314, and 316 provide support positions for the slide at each of the lobe portions. While four lobe portions are shown, embodiments of the present invention are not limited to three or four lobe portions, as the aperture 302 may include additional lobe portions. The number of lobe portions may be determined, for example, by the size of the resilient member 20. As shown in FIG. 8, the lobe portions 304, 306, 308, 310 may be arranged to provide a gradually descending configuration relative to the slot surface 36. The descending, stairstepping-like configuration may be advantageous should the clinician desire to actively ligate gradually decreasing archwire sizes or to actively ligate gradually increasing archwire sizes. For example, when the ligating slide and resilient member 20 (not shown) are in the lobe portion 304, the clinician may insert a relatively small archwire into the archwire slot 16 and then move the slide (not shown) to the lobe portion 310 to actively ligate the small archwire.

During the course of treatment, the clinician may desire to increase the archwire size, in which case the clinician, after inserting the larger archwire, may move the slide to the lobe portion 308. In this position, the slide may actively ligate the larger archwire. With continuing treatment the clinician may increase the archwire size again and actively ligate the larger archwire by moving the slide to the lobe portion 306. A similar methodology may be utilized for a gradually decreasing archwire size. In addition, it will be appreciated that the bracket 300 may be utilized for passive ligation with a change in archwire sizes. For example, where the lobe portion 310 actively ligates the archwire, the clinician may position the slide according to the lobe portion 308 to passively ligate the same archwire. Multiple combinations of active and passive ligation techniques may be utilized by combining the multiple slide positions associated with the lobe portions 304, 306, 308, and 310 in combination with multiple archwire sizes.

While the present invention has been illustrated by a description of various preferred embodiments and while these embodiments have been described in some detail, it is not the intention of the inventor to restrict or in any way limit the scope of the appended claims to such detail. Additional advantages and modifications will readily appear to those skilled in the art. By way of example, while the embodiments described herein show the resilient member pushing the ligating slide in the direction of the slide motion, the resilient members may be configured to pull the ligating slide toward the base surface of the archwire slot.

Thus, the various features of the invention may be used alone or in any combination depending on the needs and preferences of the user.

What is claimed is:

1. An orthodontic bracket for coupling an archwire with a tooth, comprising:
    a bracket body configured to be mounted to the tooth, the bracket body including an archwire slot and having a base surface that at least partly defines the archwire slot and a bracket body track surface comprising a generally planar surface having a ridge;
    a slide member movable relative to the bracket body between an opened position, a first ligating position, and a second ligating position, the slide member including a slide member track surface comprising a recess, the recess including a first wall and a second wall, wherein in the first ligating position and in the second ligating position, a surface of the slide member bounds the archwire slot on a side generally opposite to the base surface; and
    a resilient member coupled to one of the slide member and the bracket body and configured to movably engage the other of the slide member and the bracket body, the resilient member being configured to bias the slide member toward the base surface of the archwire slot in at least one of the first and second ligating positions,
    wherein in the first ligating position, the base surface of the archwire slot and the surface of the slide member are separated by a first distance and, in the second ligating position, the base surface of the archwire slot and the slide member are separated by a second distance that is different from the first distance, wherein, in the opened position, the first wall of the recess is positioned adjacent to the ridge and, in one of the first and second ligating positions, the second wall of the recess is supported on the ridge.

2. The orthodontic bracket of claim 1, wherein the resilient member is deformed when in the first ligating position such that the slide member is biased toward the base surface of the archwire slot.

3. The orthodontic bracket of claim 1, wherein the first distance is less than the second distance.

4. The orthodontic bracket of claim 1, wherein the force biasing the slide member toward the base surface of the archwire slot is greater in the first ligating position than in the second ligating position.

5. The orthodontic bracket of claim 1, wherein the resilient member is deformed when in the second ligating position such that the slide member is biased toward the base surface of the archwire slot when in the second ligating position.

6. The orthodontic bracket of claim 5, wherein the second distance is less than the first distance.

7. The orthodontic bracket of claim 1, wherein the force biasing the slide member toward the base surface of the archwire slot is greater in the second ligating position than in the first ligating position.

8. The orthodontic bracket of claim 1, wherein movement of the slide member between the opened position, the first ligating position, and the second ligating position is in a direction that is generally perpendicular to an axis of the archwire slot.

9. The orthodontic bracket of claim 1, wherein a distance of travel of the slide member generally perpendicular to an axis of the archwire slot from the opened position to the first ligating position is less than a distance of travel of the slide member generally perpendicular to the axis of the archwire slot from the opened position to the second ligating position.

10. The orthodontic bracket of claim 1, wherein the surface of the slide member is fixed relative to the base surface of the archwire slot in each of the first ligating position and the second ligating position.

11. The orthodontic bracket of claim 1, wherein the bracket body includes a wall and the slide member contacts the wall in one of the first ligating position and the second ligating position, the wall being configured to define a minimum distance between the base surface of the archwire slot and the surface of the slide member.

12. The orthodontic bracket of claim 11, wherein the slide member is configured to contact the wall in the first position.

13. The orthodontic bracket of claim 1, wherein the slide member includes at least one bore and the bracket body includes an aperture, the resilient member being movable within the aperture and being fixed within the at least one bore, wherein the aperture is asymmetric about a plane generally parallel to the base surface and has at least one dimension sized to cause the resilient member to deform during movement of the slide between the first ligating position and the second ligating position.

14. The orthodontic bracket of claim 1, wherein, in the other of the first and second ligating positions, the ridge is spaced apart from the first and second walls of the recess.

15. The orthodontic bracket of claim 1, wherein the generally planar surface is generally parallel to the base surface.

16. An orthodontic bracket for coupling an archwire with a tooth, comprising:
  a bracket body configured to be mounted to the tooth, the bracket body including an archwire slot configured to receive the archwire therein and having a base surface that at least partly defines the archwire slot;
  a slide member movable relative to the bracket body between an opened position, a first ligating position, and a second ligating position, wherein in the first ligating position and in the second ligating position, a surface of the slide member bounds the archwire slot on a side generally opposite to the base surface; and
  a resilient member coupled to one of the slide member and the bracket body and configured to movably engage the other of the slide member and the bracket body, the resilient member being configured to bias the slide member toward the base surface of the archwire slot in at least one of the first and second ligating positions,
  wherein in the first ligating position, the base surface of the archwire slot and the surface of the slide member are separated by a first distance and, in the second ligating position, the base surface of the archwire slot and the slide member are separated by a second distance that is different from the first distance,
  wherein the archwire slot further includes a first slot surface and a second slot surface extending outwardly from the base surface and the slide member has a leading edge that is adjacent the first slot surface in the opened position, between the first slot surface and the second slot surface in the first ligating position, and adjacent the second slot surface in the second ligating position.

17. A method of orthodontic treatment with a self-ligating orthodontic bracket attached to a tooth, the orthodontic bracket including a bracket body having an archwire slot formed therein and a bracket body track surface comprising a generally planar surface having a ridge, a slide member including a slide member track surface comprising a recess, the recess including a first wall and a second wall, and a resilient member coupled to one of the slide member and the bracket body and configured to engage the other of the slide member and the bracket body, and an archwire being disposed in the archwire slot, the method comprising:
  moving the slide member generally perpendicularly toward an axis of the archwire slot from a first ligating position to a second ligating position, wherein, in the first ligating position, a surface of the slide member is spaced from a base surface of the archwire slot at a first distance, the surface of the slide member opposes the base surface of the archwire slot so as to form one boundary of the archwire slot,
  wherein, in the second ligating position, the surface of the slide member is spaced from the base surface of the archwire slot at a second distance that is different from the first distance, and forms one boundary of the archwire slot,
  wherein, in one of the first ligating position and the second ligating position, the second wall of the recess is supported on the ridge,
  wherein, in one of the first ligating position and the second ligating position, the resilient member has a deformed state that biases the slide member toward the base surface of the archwire slot, and
  wherein the first ligating position includes active ligation of the archwire and the second ligating position includes passive ligation of the archwire and moving the slide member includes moving the slide member from active ligation of the archwire to passive ligation of the archwire.

18. The method of claim 17, wherein during moving of the slide member, the resilient member is deformed.

19. The method of claim 17, wherein moving the slide member to the first ligating position deforms the resilient member and the resilient member remains deformed in the first ligating position.

20. The method of claim 17, wherein moving the slide member includes moving the surface of the slide member closer to the base surface of the archwire slot.

21. The method of claim 17, wherein moving the slide member includes moving the surface of the slide member further from the base surface of the archwire slot.

22. The method of claim 17, further comprising moving the slide member from the first ligating position to an opened position in which the archwire slot is open, and removing the archwire from the archwire slot.

23. The method of claim 17, further comprising moving the slide member from the first ligating position to an opened position in which the first wall of the recess is positioned adjacent to the ridge.

24. An orthodontic bracket for coupling an archwire with a tooth, comprising:
- a bracket body configured to be mounted to the tooth, the bracket body including a base surface at least partially defining an archwire slot and a bracket body track surface comprising a generally planar surface including a shelf and a ramp intermediate the generally planar surface and the shelf;
- a slide member movable relative to the bracket body between an opened position, a first ligating position, and a second ligating position, wherein in the first ligating position and in the second ligating position, a surface of the slide member bounds the archwire slot on a side generally opposite to the base surface, wherein the slide member includes a slide member track surface including leading edge and a recess positioned proximate to the leading edge; and
- a resilient member movably coupling the slide member to the bracket body and being configured to bias the slide member toward the base surface of the archwire slot in at least one of the first and second ligating positions,
- wherein in the first ligating position, the base surface of the archwire slot and the surface of the slide member are separated by a first distance and, in the second ligating position, the base surface of the archwire slot and the slide member are separated by a second distance that is different from the first distance, and
- wherein, in the opened position, the leading edge is positioned on the generally planar surface of the bracket body track surface and, in one of the first and second ligating positions, the leading edge is positioned on the ramp of the bracket body track surface.

* * * * *